(12) United States Patent
Barth

(10) Patent No.: US 12,195,630 B2
(45) Date of Patent: Jan. 14, 2025

(54) PIGMENT INK DISPERSIONS, TATTOO INKS CONTAINING THE PIGMENT INK DISPERSIONS, AND METHOD OF MAKING THE SAME

(71) Applicant: Mario Barth, Las Vegas, NV (US)

(72) Inventor: Mario Barth, Las Vegas, NV (US)

(*) Notice: Subject to any disclaimer, the term of this patent is extended or adjusted under 35 U.S.C. 154(b) by 0 days.

(21) Appl. No.: 18/169,481

(22) Filed: Feb. 15, 2023

(65) Prior Publication Data

US 2023/0257603 A1  Aug. 17, 2023

Related U.S. Application Data

(60) Provisional application No. 63/387,574, filed on Dec. 15, 2022, provisional application No. 63/311,186, filed on Feb. 17, 2022.

(51) Int. Cl.
C09D 11/037 (2014.01)
A61K 8/04 (2006.01)
(Continued)

(52) U.S. Cl.
CPC .............. *C09D 11/037* (2013.01); *A61K 8/04* (2013.01); *A61Q 1/025* (2013.01); *C09D 11/033* (2013.01);
(Continued)

(58) Field of Classification Search
CPC ...... C09D 11/037; C09D 11/033; A61K 8/04; A61K 2800/43; A61K 2800/70; A61K 2800/91; A61Q 1/025
See application file for complete search history.

(56) References Cited

U.S. PATENT DOCUMENTS 6,013,122 A * 1/2000 Klitzman ............... A61Q 19/04
106/31.03
7,699,917 B1 * 4/2010 Pagnotta ................ C09D 11/54
106/31.03
(Continued)

FOREIGN PATENT DOCUMENTS

DE  102007060489 A1 *  6/2009 .......... A61K 8/4913
JP  2007084510 A  *  4/2007
(Continued)

OTHER PUBLICATIONS

Karregat, Joey J., et al. "Assessment of Cytotoxicity and Sensitization Potential of Intradermally Injected Tattoo Inks in Reconstructed Human Skin." Contact Dermatitis, vol. 85, No. 3, 2021, pp. 324-339, https://doi.org/10.1111/cod.13908. (Year: 2021).*
(Continued)

*Primary Examiner* — Jennifer A Smith
*Assistant Examiner* — Jeffrey Eugene Barzach
(74) *Attorney, Agent, or Firm* — Fox Rothschild LLP

(57) ABSTRACT

A pigment dispersion is disclosed incorporating a pigment selected from the group consisting of $TiO_2$ (CI 77891), Blue 15 (CI 74160), Carbon black (CI 77266), Orange 64 (CI 12760), Red 202 (CI 73907), Red 254 (CI 56110), Yellow 151 (CI 13980), Yellow 180 (CI 21290), Blue 16 (CI 74100), Blue 60 (CI 69800), Green 36 (CI 74265), Green 7 (CI 74260), and any combination thereof, a solvent, for example, *Hamamelis virginiana* Extract, and at least one additive, for example, alkyl glycosides, and having low impurity content. Also disclosed is a tattoo ink including the pigment dispersion and methods of making the pigment dispersion.

22 Claims, 7 Drawing Sheets

(51) Int. Cl.
A61Q 1/02 (2006.01)
C09D 11/033 (2014.01)
(52) U.S. Cl.
CPC ...... A61K 2800/43 (2013.01); A61K 2800/70 (2013.01); A61K 2800/91 (2013.01)

(56) References Cited

U.S. PATENT DOCUMENTS

| | | | | |
|---|---|---|---|---|
| 2002/0161104 | A1* | 10/2002 | Labrousse | A61K 8/732 524/588 |
| 2005/0287091 | A1* | 12/2005 | Kaiser | A61K 8/73 424/63 |
| 2006/0005326 | A1* | 1/2006 | Rollat-Corvol | A61Q 5/065 8/405 |
| 2008/0206465 | A1* | 8/2008 | House | C09D 11/40 427/256 |
| 2009/0170986 | A1* | 7/2009 | Brust | C09D 11/326 524/104 |
| 2010/0043151 | A1* | 2/2010 | Umeno | A61Q 5/10 8/405 |
| 2019/0231671 | A1* | 8/2019 | Lingoes | A61Q 1/02 |
| 2022/0257535 | A1* | 8/2022 | Arnold | A61K 31/045 |

FOREIGN PATENT DOCUMENTS

| | | | | |
|---|---|---|---|---|
| JP | 2007119480 | A * | 5/2007 | ........... A61K 36/605 |
| JP | 2007176815 | A * | 7/2007 | |
| JP | 2013079212 | A * | 5/2013 | |
| JP | 2015112411 | A * | 6/2015 | |
| JP | 2015127314 | A * | 7/2015 | |
| WO | WO-2010066723 | A1 * | 6/2010 | ............. A61K 8/922 |
| WO | 2017177184 | A1 | 10/2017 | |
| WO | WO-2022245758 | A1 * | 11/2022 | |
| WO | WO-2023023851 | A1 * | 3/2023 | |
| WO | WO-2023059784 | A1 * | 4/2023 | |

OTHER PUBLICATIONS

"Commission Regulation (EU) 2020/2081, Amending Annex XVII to EU Regulation No. 1907/2006." EU Regulation, Dec. 15, 2020, eur-lex.europa.eu/legal-content/EN/TXT/?uri=CELEX% 3A32020R2081. (Year: 2020).*
"Exposing What's in Tattoo Ink." American Chemical Society, Aug. 24, 2022, www.acs.org/pressroom/newsreleases/2022/august/exposing-whats-in-tattoo-ink.html. (Year: 2022).*
"Annex VI to EU Regulation No. 1272/2008." EU Regulation, Dec. 31, 2008, eur-lex.europa.eu/legal-content/EN/TXT/PDF/?uri= CELEX:32008R1272. (Year: 2008).*
"Annex II and IV of EU Regulation No. 1223/2009." EU Regulation, Dec. 22, 2009, eur-lex.europa.eu/legal-content/EN/TXT/PDF/? uri=CELEX:32009R1223. (Year: 2009).*
English Machine Translation of DE102007060489A1 ("Machine_Translation_DE_102007060489_A1") (Year: 2009).*
Beetsma, Jochum. "Optical Properties of Pigments: Absorption and Scattering." Prospector Knowledge Center, Mar. 9, 2022, www. ulprospector.com/knowledge/5871/pc-pigment-optical-properties-absorption-scattering/. (Year: 2022).*
"Carcinogenicity of some aromatic amines and related compounds." The Lancet Oncology, vol. 21, No. 8, 2020, pp. 1017-1018, https:// doi.org/10.1016/S1470-2045(20)30375-2 (Year: 2020).*
English machine translation of WO-2010066723-A1 (Year: 2010).*
English machine translation of JP-2007119480-A (Year: 2007).*
English machine translation of JP-2013079212-A (Year: 2013).*
English machine translation of JP-2007176815-A (Year: 2007).*
English machine translation of JP-2015112411-A (Year: 2015).*
English machine translation of JP-2007084510-A (Year: 2007).*
English machine translation of JP-2015127314-A (Year: 2015).*
Piccinini, P. et al., "Safety of tattoos and permanent make-up: State of play and trends in tattoo practices," JRC Science Hub (2015): 204 pages.

Serup, J. et al., "Tattooed Skin and Health," Current Problems in Dermatology (Mar. 26, 2015); 48: 270 pages.
Quality and Compliance Technical Dossier for Bright Green Lot 12192. World Famous Tattoo Ink; Limitless. Dec. 20, 2021 (7 pages).
Quality and Compliance Technical Dossier for Dark Blue 2 Lot 13952. World Famous Tattoo Ink; Limitless. Jan. 24, 2022 (1 page).
Quality and Compliance Technical Dossier for Dark Green 2 Lot 53970. World Famous Tattoo Ink; Limitless. Nov. 21, 2022 (1 page).
Quality and Compliance Technical Dossier for Dark Blue 2 v2 Lot 53966. World Famous Tattoo Ink; Limitless. Dec. 29, 2022 (1 page).
Xtreme Tattoo Inks [@xtremetattooink]. Xtreme RC Inks Announcement. Instagram, Jul. 23, 2022 (1 page).
Xtreme Tattoo Inks [@xtremetattooink]. Xtreme RC Inks Available Now. Instagram, Sep. 23, 2022 (1 page).
World Famous Tattoo Ink [@worldfamousink]. Limitless Announcement. Instagram, Dec. 27, 2021 (1 page).
World Famous Tattoo Ink [@worldfamousink]. Limitless Green Inks Announcement. Instagram, Dec. 14, 2022 (1 page).
Safety Data Sheet for Xtreme Ink. Version 7.0 date: Nov. 28, 2022, Original issue date: Dec. 12, 2019: available at https://xtremeinks. com/pages/msds-sheet (7 pages).
Intenze [@intenzetattooink]. Gen-Z Announcement. Instagram, Dec. 24, 2021 (1 page).
Intenze [@intenzetattooink]. Gen-Z Blue and Green Inks Announcement. Instagram, Dec. 15, 2022 (1 page).
Safety Data Sheet for Gen-Z Hard Orange. Jan. 13, 2022 (10 pages).
Safety Data Sheet for Gen-Z Snow White Mixing. Jan. 13, 2022 (9 pages).
Safety Data Sheet for Gen-Z Lemon Yellow. Jan. 13, 2022 (10 pages).
Safety Data Sheet for Gen-Z Golden Yellow. Jan. 13, 2022 (10 pages).
Safety Data Sheet for Gen-Z Soft Orange. Jan. 13, 2022 (10 pages).
Safety Data Sheet for Gen-Z Bright Red. Jan. 13, 2022 (10 pages).
Safety Data Sheet for Gen-Z Dark Red. Nov. 18, 2022 (10 pages).
Safety Data Sheet for Gen-Z Light Magenta. Jun. 22, 2022 (8 pages).
Safety Data Sheet for Gen-Z Snow White Opaque. Jan. 13, 2022 (10 pages).
Safety Data Sheet for Gen-Z True Magenta. Nov. 22, 2022 (11 pages).
Safety Data Sheet for Gen-Z Light Purple. Nov. 30, 2022 (11 pages).
Safety Data Sheet for Gen-Z Dark Purple. Nov. 30, 2022 (11 pages).
Safety Data Sheet for Gen-Z Mario's Blue. Dec. 21, 2022 (10 pages).
Safety Data Sheet for Gen-Z Light Green. Dec. 19, 2022 (10 pages).
Safety Data Sheet for Gen-Z Dark Brown. Nov. 29, 2022 (10 pages).
Safety Data Sheet for Gen-Z Dark Green. Dec. 19, 2022 (10 pages).
Safety Data Sheet for Gen-Z True Black. Jan. 13, 2022 (10 pages).
Safety Data Sheet for Gen-Z Rose Pink. Jan. 14, 2022 (10 pages).
Safety Data Sheet for Gen-Z Light Brown. Dec. 20, 2022 (10 pages).
Safety Data Sheet for Gen-Z Banana Cream. Jan. 14, 2022 (12 pages).
Safety Data Sheet for Gen-Z Bahama Blue. Dec. 19, 2022 (10 pages).
Safety Data Sheet for Gen-Z Baby Blue. Dec. 19, 2022 (10 pages).
Safety Data Sheet for Gen-Z Creamsicle. Jan. 14, 2022 (12 pages).
Safety Data Sheet for Gen-Z Just Pink. Jan. 14, 2022 (12 pages).
Safety Data Sheet for Gen-Z Lavender. Nov. 30, 2022 (10 pages).
Safety Data Sheet for Gen-Z Peach. Jan. 14, 2022 (12 pages).
Safety Data Sheet for Gen-Z Platinum. Jan. 14, 2022 (13 pages).
Safety Data Sheet for Gen-Z Blue Sky. Nov. 30, 2022 (10 pages).
Safety Data Sheet for Gen-Z Sea Foam Green. Dec. 19, 2022 (10 pages).
Safety Data Sheet for Gen-Z Lining Black. Jan. 14, 2022 (12 pages).
Safety Data Sheet for Gen-Z Gray Wash Dark. Jan. 14, 2022 (11 pages).
Safety Data Sheet for Gen-Z Gray Wash Medium. Jan. 14, 2022 (11 pages).
Safety Data Sheet for Gen-Z Gray Wash Light. Jan. 14, 2022 (11 pages).

(56) References Cited

OTHER PUBLICATIONS

Safety Data Sheet for Gen-Z Black Sumi. Jan. 14, 2022 (12 pages).
Safety Data Sheet for Gen-Z Zuper Black. Jan. 14, 2022 (22 pages).
Safety Data Sheet for Gen-Z Special Shading Solution. Feb. 2, 2022 (10 pages).
Safety Data Sheet for Gen-Z Lining Red Light. Jan. 14, 2022 (11 pages).
Safety Data Sheet for Gen-Z Lining Red Dark. Dec. 20, 2022 (10 pages).
Safety Data Sheet for Gen-Z Lining Green. Dec. 20, 2022 (10 pages).
Safety Data Sheet for Gen-Z Lining Brown Dark. Dec. 20, 2022 (10 pages).
Safety Data Sheet for Gen-Z Lining Brown Light. Dec. 20, 2022 (10 pages).
Safety Data Sheet for Gen-Z Lining Blue Dark. Dec. 19, 2022 (10 pages).
Safety Data Sheet for Gen-Z Lining Blue Light. Dec. 19, 2022 (10 pages).
Safety Data Sheet for Gen-Z Lining Magenta. Jan. 14, 2022 (10 pages).
Safety Data Sheet for Gen-Z Lining Purple. Dec. 20, 2022 (10 pages).
Safety Data Sheet for Gen-Z Dark Tone. Jan. 14, 2022 (9 pages).
Safety Data Sheet for Gen-Z Lining Yellow. Jan. 14, 2022 (10 pages).
Safety Data Sheet for Gen-Z Medium Tone. Jan. 14, 2022 (11 pages).
Safety Data Sheet for Gen-Z Light Tone. Jan. 14, 2022 (11 pages).
Safety Data Sheet for Gen-Z Dimension Black. Jan. 17, 2022 (10 pages).
Safety Data Sheet for Gen-Z Sculpting Black. Jan. 14, 2022 (11 pages).
Safety Data Sheet for Gen-Z High White. Jan. 17, 2022 (12 pages).
Safety Data Sheet for Gen-Z Let There Be Light. Jan. 14, 2022 (10 pages).
Safety Data Sheet for Gen-Z Extra Medium. Jan. 14, 2022 (11 pages).
Safety Data Sheet for Gen-Z Dark And Lovely. Jan. 14, 2022 (12 pages).
Safety Data Sheet for Gen-Z Black Velvet. Jan. 14, 2022 (9 pages).
Safety Data Sheet for Gen-Z White Silk. Jan. 14, 2022 (9 pages).
Safety Data Sheet for Gen-Z Miracle Water. Jan. 17, 2022 (8 pages).
Safety Data Sheet for Gen-Z Formula 23 Original. Feb. 1, 2022 (12 pages).
Safety Data Sheet for Gen-Z Lamp Black. Jan. 17, 2022 (10 pages).
Safety Data Sheet for Gen-Z Coal. Dec. 20, 2022 (11 pages).
Safety Data Sheet for Gen-Z Slate. Jan. 17, 2022 (10 pages).
Safety Data Sheet for Gen-Z Grandpa Grey. Jan. 17, 2022 (9 pages).
Safety Data Sheet for Gen-Z Pure Blue. Nov. 30, 2022 (10 pages).
Safety Data Sheet for Gen-Z Dark Blue. Nov. 30, 2022 (10 pages).
Safety Data Sheet for Gen-Z Nosta White. Dec. 20, 2022 (10 pages).
Safety Data Sheet for Gen-Z Blue Water. Nov. 30, 2022 (10 pages).
Safety Data Sheet for Gen-Z Retro. Dec. 20, 2022 (11 pages).
Safety Data Sheet for Gen-Z Graphit. Dec. 20, 2022 (11 pages).
Safety Data Sheet for Gen-Z Light Blue. Nov. 30, 2022 (10 pages).
Safety Data Sheet for Gen-Z Pure Green. Nov. 30, 2022 (10 pages).
Safety Data Sheet for Gen-Z Dark Grass. Nov. 30, 2022 (10 pages).
Safety Data Sheet for Gen-Z Camouflage. Nov. 30, 2022 (10 pages).
Safety Data Sheet for Gen-Z Medium Grass. Nov. 30, 2022 (10 pages).
Safety Data Sheet for Gen-Z Light Grass. Nov. 30, 2022 (10 pages).
Sadura, F. et al., "Application of Raman Spectroscopy for the Detection of Colored Tattoo Inks in Tissues: Preliminary Phantom Study," Translational Biophotonics: Diagnostics and Therapeutics (2021); 11919: 3 pages.
Zanovello, U. et al., "Experimental procedure for EM characterization of tattoo inks in the framework of potential MRI interactions," Measurement (2020); 158(29): 9 pages.
Giulbudagian, M. et al., "Safety of tattoos and permanent make-up: a regulatory view," Archives of Toxicology (2020); 94(2): pp. 357-369.

\* cited by examiner

PIGMENT INK DISPERSIONS, TATTOO INKS CONTAINING THE PIGMENT INK DISPERSIONS, AND METHOD OF MAKING THE SAME

CROSS-REFERENCE TO RELATED APPLICATIONS

This application claims the benefit of priority to U.S. Provisional Patent Application No. 63/387,574, filed on Dec. 15, 2022, and U.S. Provisional Patent Application No. 63/311,186, filed on Feb. 17, 2022. The entire contents of each of the foregoing applications are hereby incorporated by reference herein.

FIELD OF THE DISCLOSURE

The disclosure relates to novel pigment ink dispersions for tattoo ink having minimized impurities and methods of making the pigment dispersions.

BACKGROUND OF THE DISCLOSURE

In 2000, the Scientific Committee on Cosmetic Products and Non-Food Products delivered an opinion regarding the safety of tattoos. The committee recommended that a systematic effort be undertaken to amass chemical and toxicological information so that a thorough risk assessment could be conducted. Blass Rico, A. M., "EU Actions to Ensure the Safety of Tattoos and the Protection of Consumers," Serup J, Kluger N, Bäumler W (eds): Tattooed Skin and Health, Curr Probl Dermatol. Basel, Karger, 2015, vol 48, pp 206-209 (DOI: 10.1159/000369229). The European Commission (EC) established a common knowledge basis on the safety of tattoos and body piercing, including collecting and assessing information on consumer exposure to chemicals in consumer products and articles and associated health risks. The work resulted in a report summarizing the conclusions and recommendations for regulatory action on the safety of tattoos, body piercing, and related practices in the EU.

The Resolution of the Council of Europe in 2008 (ResAP (2008)) set up the basis for the safety of tattoo products, including requirements and criteria for the safety of tattoos and permanent make-up in order to increase the level of consumer health protection. Tattoo products are injected into the skin and may represent a risk to human health due to possible microbiological contamination and/or contamination by the presence of hazardous substances in the products. Verdier, C., "Surveillance of Tattoo-Related Adverse Events by the EU RAPEX System and by National Monitoring," Serup J, Kluger N, Bäumler W (eds): Tattooed Skin and Health. Curr Probl Dermatol. Basel, Karger, 2015, vol 48, pp 210-217 (DOI: 10.1159/000369230).

Tattoos cause a broad range of clinical problems. Mild adverse effect, in particular sensitivity to sun, are common and occur in about 20% of cases. Medical complications, such as allergic responses to tattoo pigment, especially in red but also in blue and green tattoos, also occur. Tattoo allergies and local reactions show distinct clinical manifestations, with plaque-like, excessive hyperkeratotic, ulcero-necrotic, lymphopathic, neuro-sensory, and scar patterns. Reactions in black tattoos are papulo-nodular and non-allergic and associated with the agglomeration of nanoparticulate carbon black. Tattoo complications include effects on general health conditions and complications in the psycho-social sphere. Bacterial contamination and infections, especially staphylococci, from tattooing may also occur, and in some cases may be resistant to certain antibiotics.

Tattooing is a single-dose injection of a large local dose, depending on the size of the tattoo. Tattoo inks contain soluble ingredients, which are understood to be distributed, metabolized, and excreted from the body within a few days. However, the pigment particles remain permanently in the skin to provide the desired coloring. Pigments in the skin slowly vanish over time, along with a slow release of minute amounts of chemicals and metabolites, which may actually cause adverse reactions, such as an allergy. Serup, J. et al., "Tattoo Complaints and Complications: Diagnosis and Clinical Spectrum," Serup J, Kluger N, Bäumler W (eds): Tattooed Skin and Health. Curr Probl Dermatol. Basel, Karger, 2015, vol 48, pp 48-60 (DOI: 10.1159/000369645). The release is triggered by enzymatic and cellular processes in the tissues that are very different from harsh chemical degradation, with the formation of chemical cleavage products, in the Laboratory, which is an artificial and unrealistic scenario. Id. Pigments instilled into the tattoo partly escape via the lymph and become deposited in the regional lymph nodes. Id. The nodes are invisibly dyed along with the skin. Id. However, unknown amounts of pigment nanoparticles might reach the blood stream and theoretically cause harm somewhere in the body. Id.

It has been documented that many tattoo inks, as referenced to register data, contain carcinogenic, mutagenic, and reprotoxic substances. Id. However, concerns about tattoos' induction of skin cancer, including malignant melanoma, have not been confirmed in the medical literature and remain hypothetical. Id.

New inks and pigments are needed to address the potential health and safety issues of tattooing.

SUMMARY OF THE DISCLOSURE

A pigment dispersion is disclosed containing: a pigment selected from the group consisting of $TiO_2$ (CI 77891), Blue 15 (CI 74160), Carbon black (CI 77266), Orange 64 (CI 12760), Red 202 (CI 73907), Red 254 (CI 56110), Yellow 151 (CI 13980), Yellow 180 (CI 21290), Blue 16 (CI 74100), Blue 60 (CI 69800), Green 36 (CI 74265), Green 7 (CI 74260), or any combination thereof; one or more solvents; and one or more additives. The pigment may be selected from the group consisting of Blue 16, Blue 60, Green 36, Green 7, or any combination thereof. The one or more solvents may be selected from the group consisting of *Hamamelis virginiana* Extract, ethyl alcohol, water, or any combination thereof. The one or more solvent may be *Hamamelis virginiana* Extract. The one or more additives is selected from a group consisting of: an antifoaming agent, a dispersant, a binding agent, a humectant, a wetting agent, and any combination thereof. The pigment dispersion may include the pigment, optionally in about 30 wt. % to about 60 wt. % of the total weight of the pigment dispersion, *Hamamelis virginiana* Extract; ethyl alcohol; simethicone; ammonium acrylates copolymer; glycerine; polyethylene glycol; alkyl polyglycosides; and water.

The pigment dispersion may contain less than about 5 ppm of free aromatic amines listed in Table 4. The pigment dispersion may contain: less than about 0.5 ppm of mercury, organometallic tin, antimony, arsenic, cadmium, chromium (Cr(VI)), or any combination thereof; less than about 0.7 ppm of lead; less than about 5 ppm of nickel; less than about 500 ppm of barium; less than about 250 ppm of copper; less than about 2 ppm of selenium; less than about 2000 ppm of zinc; and/or less than 0.005 ppm of benz[a]pyrene. The pigment dispersion may contain less than about 0.5 ppm of one or more of the polyaromatic hydrocarbons listed in Table 3. The particle size range of the pigment dispersion may be about 150 nm to about 15 μm, and/or the particle size distribution D90 of the pigment dispersion may be less than about 6 μm, or less than about 5 μm.

A tattoo ink formulation comprising the pigment dispersion: at least one solvent; and at least one additive. The pigment dispersion comprises less than about 95 wt. % of the tattoo ink formulation. The tattoo ink formulation may contain: about 1 wt. % to about 95 wt,% of the pigment dispersion; about 1 wt. % to about 50 wt. % of *Hamamelis virginiana* Extract; and about 1 wt. % to about 50 wt. % water; and optionally less than about 5 wt. % of impurities. The tattoo ink formulation may contain: less than or equal to about 0.5 ppm total polycyclic aromatic hydrocarbons; less than or equal to about 10 ppm benzo[a]pyrene (BaP); less than or equal to about 10 ppm dibenz[a,h]anthracene (DBA); less than or equal to about 3 ppm arsenic; less than or equal to about 1 ppm mercury; and/or less than or equal to about 10 ppm lead.

Methods of making the pigment dispersion are also disclosed. A method comprises mixing the pigment, one or more solvents, and one or more additives using a high shear mixer for a period of about 30 minutes to about 4 hours at a speed of about 1,000 feet per minute to about 20,000 feet per minute. Another method of making a pigment dispersion comprises: combining at least one solvent selected from the group consisting of *Hamamelis virginiana* Extract, ethyl alcohol, water, or any combination thereof; simethicone; glycerine; a dispersant; and one or more additives, to make a solution; mixing the solution to make a homogenous mixture; adding a pigment to the homogenous mixture and mixing in a high shear mixer at about 2000 RPM to about 4000 RPM for about 1 hour to about 4 hours at a temperature of about 68° F. to about 110° F. to make a homogenous pigment dispersion. A method of making a pigment dispersion with powder induction is also disclosed, which includes mixing the homogenous mixture at about 3000 RPM to about 4000 RPM in an in-line high shear mixer for about 1 hour to about 4 hours at a temperature of about 68° F. to about 110° F. while adding a pigment to the homogenous mixture through a powder induction system comprising a vacuum pump, wherein the powder induction system is coupled to an in-line high shear mixer, to make a homogenous pigment dispersion.

DETAILED DESCRIPTION OF THE DISCLOSURE

Figure 1:
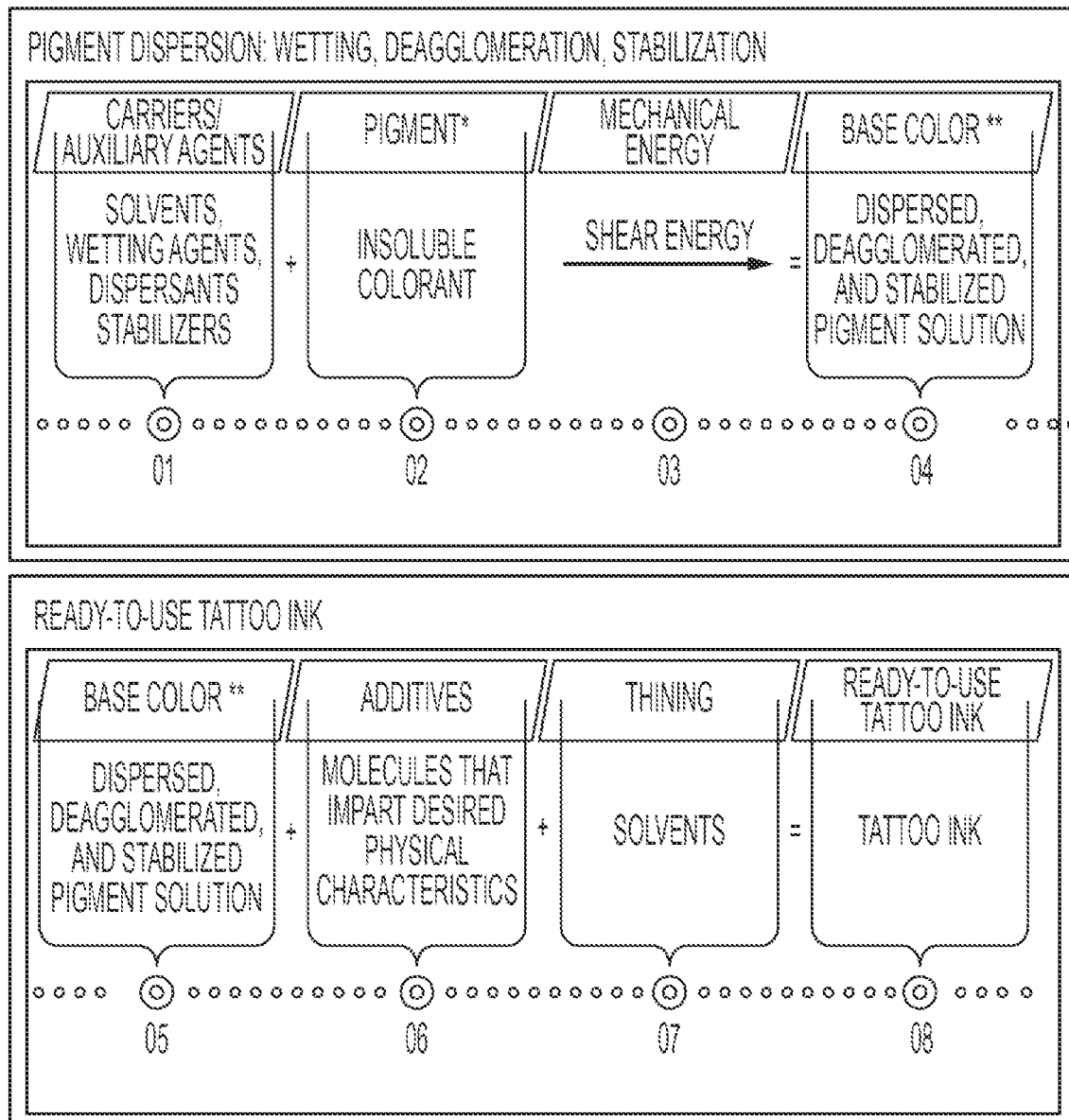
FIG. 1 is a flowchart showing the different ingredients mixed into a base color and a base color formulated into a tattoo ink.

Pigment dispersions disclosed herein comprise a pigment, one or more additives, and one or more solvents. The additive(s) impart desired properties on the pigment dispersion, while the solvent thins the pigment dispersion. FIG. 1 shows processing steps for creating tattoo inks for humans. The pigment dispersion may comprise at least one pigment, at least one solvent and at least one additive. The additive may be selected from the group consisting of: a wetting agent, a dispersant, a humectant, an antifoaming agent, and any combination thereof. The solvent and the additive may be any solvent, wetting agent, dispersant, humectant, and antifoaming agent known in the art for use in processing tattoo inks.

The pigment dispersion may include a pigment, at least one solvent, one or more additives, and an antifoaming agent. The solvent may be selected from the group consisting of *Hamamelis virginiana* Extract, ethyl alcohol, water, or any combination thereof. The solvent may be *Hamamelis virginiana* Extract, ethyl alcohol, and water. *Hamamelis virginiana* Extract may also be referred to as witch hazel extract. *Hamamelis virginiana* Extract may be added to soothe the skin and ameliorate inflammation, and may have antibacterial properties. *Hamamelis virginiana* Extract used herein may be Standard USP grade witch hazel extract, which contains 14% ethanol.

The wetting agent, also referred to as a surfactant, may be any substance that lowers the surface tension of the solvent or mixture, thereby allowing formation of a pigment dispersion. Common wetting agents include ionic surfactants (e.g., sodium lauryl sulfate) as well as nonionic surfactants (e.g., alkyl phenol ethoxylate, alkyl polyglycosides). The wetting agent may be selected from the group consisting of fatty acids, sodium lauryl sulfate, quaternary ammonium salts, fatty acid alkoxylates, alkyl polyglycosides, ethoxylated fatty alcohols, and any combination thereof. The wetting agent may be an alkyl polyglycoside. The alkyl polyglycoside may be selected from the group consisting of: D-Glucopyranose, oligomers, decyl octyl glycosides; D-Glucopyranose, oligomeric, C10-16-alkyl glycosides; and any combination thereof.

The antifoaming agent may be a silicone-based fluid or emulsion, such as but not limited to simethicone, or any other antifoaming agent known for use in the art with tattoo pigments and inks to prevent bubbles and foam from forming in the ink.

The dispersant, also referred to as a stabilizer, may be any polymer known in the art that stabilizes the dispersed pigment particles either by electrostatic and/or steric interactions. The dispersant may be a polyphosphates polymer, polyacrylate salt, acrylic copolymer, polyurethane polymer, polyethylene glycol (PEG) polymer, polyvinylpyrrolidone (PVP) polymer, ammonium acrylates copolymer, alkyl polyglycoside, or any combination thereof. The pigment dispersion may include ammonium acrylates copolymer that regulates the viscosity of the pigment, and makes inserting the tattoo ink into the skin easier by giving it a "silkier" texture.

The pigment dispersion may include a humectant. The humectant may prevent drying of the ink and improve redispersibility of colorants. The humectant is also added to help hydrate skin to prevent skin's moisture loss and keep the newly tattooed skin from drying out. The humectant may be glycerine, propylene glycol, hyaluronic acid, salicylic acid, sorbitol, and any combination thereof.

The pigment dispersion may include one of more of the following: fatty acid alkoxylates (for example, in about 1 wt. % to about 10 wt. %), ethoxylated fatty alcohols (for example, in about 1 wt. % to about 10 wt. %), fatty acids (for example, in about 1 wt. % to about 10 wt. %), sodium lauryl sulfate (for example, in about 1 wt. % to about 10 wt. %), quaternary ammonium salts (for example, in about 1 wt. % to about 10 wt. %), disodium deceth-6 sulfosuccinate (for example, in about 1 wt. % to about 10 wt. %), modified acrylic polymers (for example, in about 1 wt. % to about 20 wt. %), sorbitol (for example, in about 1 wt. % to about 10 wt. %), benzyl alcohol (for example, in about 1 wt. % to about 10 wt. %), polyethylene glycol (PEG) polymer (for example, in about 1 wt. % to about 20 wt. %), polysorbate 80 (for example, in about 1 wt. % to about 20 wt. %), polysorbate 20 (for example, in about 1 wt. % to about 20 wt. %), polyvinyl pyrrolidone (PVP) polymer (for example, in about 1 wt. % to about 20 wt. %), vinyl acetate polymer (for example, in about 1 wt. % to about 20 wt. %), polyethylene-polypropylene glycol polymer (for example, in about 1 wt. % to about 20 wt. %), styrene/acrylic copolymers (for example, in about 1 wt. % to about 20 wt. %), PVP/vinyl acetate copolymer (for example, in about 1 wt. % to about 20 wt. %); and any combination thereof.

Pigments are natural or synthetic insoluble colorants that are used to impart visual properties on a wide range of products. The pigment used herein may be Black 7, Blue 15, Blue 16, Blue 60, Blue 79, Green 7, Green 36, Red 101, Red 170, Red 185, Red 238, Red 202, Red 254, Red 266, Orange 36, Orange 64, Orange 73, Violet 55, Yellow 42, Yellow 138, Yellow 151, Yellow 155, Yellow 180, White 6, or any combination thereof. The pigment used herein may be Acid Blue 9 lake, Acid Yellow 23 lake, Acid Red 18 lake, or any combination thereof. The pigment used in the pigment dispersions herein may be in powder form and selected from $TiO_2$ (CI 77891), Blue 15 (CI 74160), Blue 16 (CI 74100), Blue 60 (CI 69800), Green 36 (CI 74265), Green 7 (CI 74260), Carbon black (CI 77266), Orange 64 (CI 12760), Red 202 (CI 73907), Red 254 (CI 56110), Yellow 151 (CI 13980), Yellow 180 (CI 21290), or any combination thereof.

The black pigment may comprise carbon black which consists of elemental carbon in a paracrystalline form. Carbon black may also be known as Black 7, furnace black or High Purity Furnace Black, CI 77266, and has a Chemical Abstract Service (CAS) Registration Number: 1333-86-4. The blue pigment may comprise Blue 16 (CI 74100), Blue 60 (CI 69800), and/or Blue 15, also known as Blue 15:3, CI 74160, and Blue Phthalocyanine, and has a Chemical Abstract Service (CAS) Registration Number: 147-14-8. The white pigment may comprise $TiO_2$, White 6, CI 77891, and has a Chemical Abstract Service (CAS) Registration Number: 0.13463-67-7 The orange pigment may comprise Orange 64 (CI 12760), and has a Chemical Abstract Service (CAS) Registration Number: 72102-84-2. The magenta pigment may comprise Red 202 (CI 73907), and has a Chemical Abstract Service (CAS) Registration Number: 3089-17-6.

The red pigment may comprise Red 254 (CI 56110), and has a Chemical Abstract Service (CAS) Registration Number: 84632-65-5. The yellow pigment may comprise one of Yellow 151 (CI 13980), Yellow 180 (CI 21290), having a Chemical Abstract Service (CAS) Registration Number: 31837-42-0, and 77804-81-0, respectively. The green pigment may comprise Green 36 (CI 74265), Green 7 (CI 74260), or a combination thereof. The green pigment may comprise a mixture of Yellow 151 (CI 13980), and Blue 16 (CI 74100), Blue 60 (CI 69800), or a combination thereof. Green 36 has the following chemical structure:

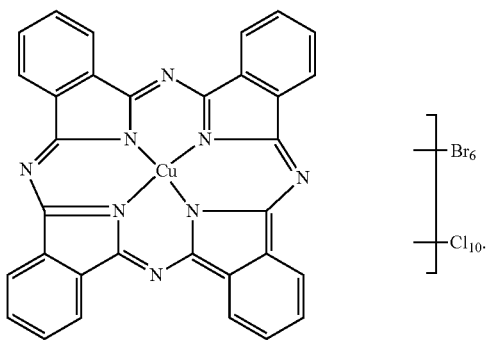

Green 7 has the following chemical structure:

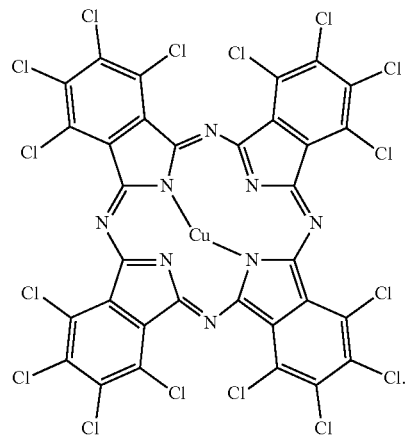

Blue 16 has the following chemical structure:

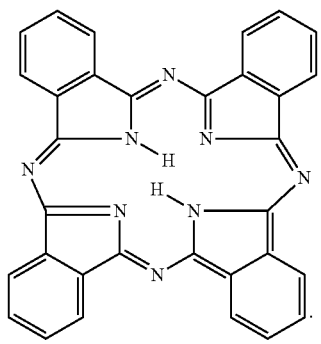 [SMILES: c1ccc2c(c1)-c1nc-2nc2[nH]c(nc3nc(nc4[nH]c(n1)c1ccccc41)-c1ccccc1-3)c1ccccc21]

Blue 60 has the following chemical structure:

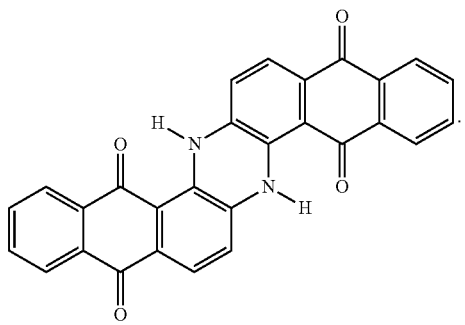 [SMILES: O=c1c2ccccc2c(=O)c2c1ccc1[nH]c3c(ccc4c(=O)c5ccccc5c(=O)c43)[nH]c12]

To deliver the pigment to the desired substrate (skin) the pigment must be transported in a liquid form using carrier molecules. The smallest base unit of a pigment is referred to as the primary particle. During the manufacturing process, primary particles are fused together through covalent bonds to form aggregates. Aggregates further self-assemble to form larger structures called agglomerates. Pigments, by definition, are insoluble in the carrier system used and must be dispersed by using both mechanical forces and auxiliary agents. The dispersion process involves three steps that happen somewhat concurrently. For the pigment to become distributed throughout the carrier system, the entire pigment surface area must be exposed to the carrier solvent. This step is referred to as "wetting" the pigment. Since pigments are insoluble in the carrier solvent system the use of wetting agents is required. A wetting agent is any additive that lowers the surface tension of the liquid dispersing medium to allow for displacement of the solid-air interface. Most wetting agents are low-molecular weight amphiphilic substances.

To form an evenly distributed dispersion, the pigment must be broken down into the aggregate particles. This step is referred to as "deagglomeration." The main forces that must be overcome during deagglomeration are Van der Waals and electrostatic interactions between pigment aggregates. This is accomplished mostly by inserting mechanical forces (impact and shear forces). Special additives may also help lower the energy needed to separate agglomerates. For the most part, aggregates remain intact during dispersion and dictate visual properties of pigment dispersion.

Once dispersed, the pigment aggregates exist in an unstable state. The dispersed pigment particles must be stabilized using dispersants. Dispersants stabilize the separated pigment particles by two main methods: electrostatic stabilization and steric stabilization. Electrostatic stabilization involves surrounding ionic pigments with poly ionic dispersants. For dispersion of inorganic based pigments electrostatic stabilization is the most important factor. Steric stabilization involves using dispersants with bulky functional groups that prevent dispersed pigment particles from coming into close contact with one another. Most dispersants are oligomers or polymers and can often stabilize dispersion by both methods.

Once the pigment is dispersed and stabilized, it is considered an ink and is ready to be used for tattooing. For the purposes of this report, we have defined a base color composition tattoo ink as any ink dispersion containing only one pigment. Although tattoos can be created using a single base color, it is very common for tattoo artists to thin or mix several base colors to obtain the desired visual properties in a tattoo ink. To accommodate for this, most tattoo ink manufacturers sell tattoo ink as pre-mixed ink dispersions containing several colorants.

The pigment dispersion, or white pigment dispersion, may include $TiO_2$ (CI 77891), one or more solvents, and one or more additives. The solvents may be *Hamamelis virginiana* Extract, ethyl alcohol, water, or any combination thereof. The solvents may be *Hamamelis virginiana* Extract, ethyl alcohol, and water. The additives may be selected from a group consisting of: an antifoaming agent (e.g., simethicone), a dispersant (e.g., ammonium acrylates copolymer), a binding agent, a humectant (e.g. glycerine), a wetting agent (e.g., alkyl polyglycoside), and any combination thereof. The white pigment dispersion may include $TiO_2$ (CI 77891), one or more solvents, an antifoaming agent (e.g., simethicone), a dispersant (e.g., ammonium acrylates copolymer), a binding agent, a humectant (e.g. glycerine), and one or more additives. The white pigment dispersion may include $TiO_2$ (CI 77891), *Hamamelis virginiana* Extract, ethyl alcohol, water, simethicone, ammonium acrylates copolymer, glycerine, polyethylene glycol, one or more alky polyglycoside, and, optionally, one or more additional additives. The white pigment dispersion may include $TiO_2$ (CI 77891), *Hamamelis virginiana* Extract, ethyl alcohol, water, simethicone, ammonium acrylates copolymer, glycerine, polyethylene glycol, D-Glucopyranose, oligomers, decyl octyl glycosides, and D-Glucopyranose, oligomeric, C10-16-alkyl glycosides. The white pigment dispersion may have a viscosity of about 500 cP to about 2000 cP as measured using any standard viscometer, which may also be referred to as a viscosity meter or rheometer, e.g., Viscolite 700 portable viscometer.

The pigment dispersion, or blue pigment dispersion, may include: a pigment selected from Blue 15 (CI 74160), Blue 16 (CI 74100), Blue 60 (CI 69800), and a combination thereof; one or more solvents; and one or more additives. The solvents may be *Hamamelis virginiana* Extract, ethyl alcohol, water, or any combination thereof. The solvents may be *Hamamelis virginiana* Extract, ethyl alcohol, and water. The additives may be selected from a group consisting of: an antifoaming agent (e.g., simethicone), a dispersant (e.g., ammonium acrylates copolymer), a binding agent, a humectant (e.g. glycerine), a wetting agent (e.g., alkyl polyglycoside), and any combination thereof. The blue pigment dispersion may include a pigment selected from Blue 15 (CI 74160), Blue 16 (CI 74100), Blue 60 (CI 69800), and a combination thereof; one or more solvents; an antifoaming agent (e.g., simethicone); a dispersant (e.g., ammonium acrylates copolymer); a binding agent; a humectant (e.g. glycerine); and one or more additives. The blue pigment dispersion may include Blue 15 (CI 74160), *Hamamelis virginiana* Extract, ethyl alcohol, water, simethicone, ammonium acrylates copolymer, glycerine, polyethylene glycol, alkyl polyglycoside, and, optionally, one or more additional additives. The blue pigment dispersion may include Blue 15 (CI 74160), *Hamamelis virginiana* Extract, ethyl alcohol, water, simethicone, ammonium acrylates copolymer, glycerine, polyethylene glycol, D-Glucopyranose, oligomers, decyl octyl glycosides, and D-Glucopyranose, oligomeric, C10-16-alkyl glycosides. The Blue 15 pigment dispersion may have a viscosity of about 20 cP to about 100 cP as measured using any standard viscometer, which may also be referred to as a viscosity meter or rheometer, e.g., Viscolite 700 portable viscometer.

The blue pigment dispersion may include Blue 16 (CI 74100), *Hamamelis virginiana* Extract, ethyl alcohol, water, simethicone, ammonium acrylates copolymer, glycerine, polyethylene glycol, alkyl polyglycoside, and, optionally, one or more additional additives. The blue pigment dispersion may include Blue 16 (CI 74100), *Hamamelis virginiana* Extract, ethyl alcohol, water, simethicone, ammonium acrylates copolymer, glycerine, polyethylene glycol, D-Glucopyranose, oligomers, decyl octyl glycosides, and D-Glucopyranose, oligomeric, C10-16-alkyl glycosides. The Blue 16 (CI 74100) pigment dispersion may have a viscosity of about 20 cP to about 200 cP as measured using any standard viscometer.

The blue pigment dispersion may include Blue 60 (CI 69800), *Hamamelis virginiana* Extract, ethyl alcohol, water, simethicone, ammonium acrylates copolymer, glycerine, polyethylene glycol, alkyl polyglycoside, and, optionally, one or more additional additives. The blue pigment dispersion may include Blue 60 (CI 69800), *Hamamelis virginiana* Extract, ethyl alcohol, water, simethicone, ammonium acrylates copolymer, glycerine, polyethylene glycol, D-Glucopyranose, oligomers, decyl octyl glycosides, and D-Glucopyranose, oligomeric, C10-16-alkyl glycosides. The Blue 60 (CI 69800) pigment dispersion may have a viscosity of about 20 cP to about 100 cP as measured using any standard viscometer.

The pigment dispersion, or green pigment dispersion, may include: a pigment selected from Green 36 (CI 74265), Green 7 (CI 74260), Yellow 151 (CI 13980), Blue 16 (CI 74100), Blue 60 (CI 69800), and any combination thereof; one or more solvents; and one or more additives. The solvents may be *Hamamelis virginiana* Extract, ethyl alcohol, water, or any combination thereof. The solvents may be *Hamamelis virginiana* Extract, ethyl alcohol, and water. The additives may be selected from a group consisting of: an antifoaming agent (e.g., simethicone), a dispersant (e.g., ammonium acrylates copolymer), a binding agent, a humectant (e.g. glycerine), a wetting agent (e.g., alkyl polyglycoside), and any combination thereof. The green pigment dispersion may include a pigment selected from Green 36 (CI 74265), Green 7 (CI 74260), Yellow 151 (CI 13980), Blue 16 (CI 74100), Blue 60 (CI 69800), and any combination thereof; one or more solvents; an antifoaming agent (e.g., simethicone); a dispersant (e.g., ammonium acrylates copolymer); a binding agent; a humectant (e.g. glycerine); and one or more additives. The green pigment dispersion may include Green 36 (CI 74265), *Hamamelis virginiana* Extract, ethyl alcohol, water, simethicone, ammonium acrylates copolymer, glycerine, polyethylene glycol, alkyl polyglycoside, and, optionally, one or more additional additives. The green pigment dispersion may include Green 36 (CI 74265), *Hamamelis virginiana* Extract, ethyl alcohol, water, simethicone, ammonium acrylates copolymer, glycerine, polyethylene glycol, D-Glucopyranose, oligomers, decyl octyl glycosides, and D-Glucopyranose, oligomeric, C10-16-alkyl glycosides. The Green 36 pigment dispersion may have a viscosity of about 20 cP to about 200 cP as measured using any standard viscometer, which may also be referred to as a viscosity meter or rheometer, e.g., Viscolite 700 portable viscometer.

The green pigment dispersion may include Yellow 151 (CI 13980) and Blue 16 (CI 74100), and/or Blue 60 (CI 69800), *Hamamelis virginiana* Extract, ethyl alcohol, water, simethicone, ammonium acrylates copolymer, glycerine, polyethylene glycol, alkyl polyglycoside, and, optionally, one or more additional additives. The green pigment dispersion may include Yellow 151 (CI 13980) and Blue 16 (CI 74100), and/or Blue 60 (CI 69800), *Hamamelis virginiana* Extract, ethyl alcohol, water, simethicone, ammonium acrylates copolymer, glycerine, polyethylene glycol, D-Glucopyranose, oligomers, decyl octyl glycosides, and D-Glucopyranose, oligomeric, C 10-16-alkyl glycosides.

The green pigment dispersion may include Green 7 (CI 74260), *Hamamelis virginiana* Extract, ethyl alcohol, water, simethicone, ammonium acrylates copolymer, glycerine, polyethylene glycol, alkyl polyglycoside, and, optionally, one or more additional additives. The blue pigment dispersion may include Green 7 (CI 74260), *Hamamelis virginiana* Extract, ethyl alcohol, water, simethicone, ammonium acrylates copolymer, glycerine, polyethylene glycol, D-Glucopyranose, oligomers, decyl octyl glycosides, and D-Glucopyranose, oligomeric, C10-16-alkyl glycosides. The Green 7 pigment dispersion may have a viscosity of about 20 cP to about 200 cP as measured using any standard viscometer, which may also be referred to as a viscosity meter or rheometer, e.g., Viscolite 700 portable viscometer.

The pigment dispersion, or black pigment dispersion, may include Carbon black (CI 77266), one or more solvents, and one or more additives. The solvents may be *Hamamelis virginiana* Extract, ethyl alcohol, water, or any combination thereof. The solvents may be *Hamamelis virginiana* Extract, ethyl alcohol, and water. The additives may be selected from a group consisting of: an antifoaming agent (e.g., simethicone), a dispersant (e.g., ammonium acrylates copolymer), a binding agent, a humectant (e.g. glycerine), a wetting agent (e.g., alkyl polyglycoside), and any combination thereof. The black pigment dispersion may include Carbon black (CI 77266), one or more solvents, an antifoaming agent (e.g., simethicone), a dispersant (e.g., ammonium acrylates copolymer), a binding agent, a humectant (e.g. glycerine), and one or more additives. The black pigment dispersion may include Carbon black (CI 77266), *Hamamelis virginiana* Extract, ethyl alcohol, water, simethicone, ammonium acrylates copolymer, glycerine, polyethylene glycol, alkyl polyglycoside, and, optionally, one or more additional additives. The black pigment dispersion may include Carbon black (CI 77266), *Hamamelis virginiana* Extract, ethyl alcohol, water, simethicone, ammonium acrylates copolymer, glycerine, polyethylene glycol, D-Glucopyranose, oligomers, decyl octyl glycosides, and D-Glucopyranose, oligomeric, C10-16-alkyl glycosides. The black pigment dispersion may have a viscosity of about 5 cP to about 50 cP as measured using any standard viscometer, which may also be referred to as a viscosity meter or rheometer, e.g., Viscolite 700 portable viscometer.

The pigment dispersion, or orange pigment dispersion, may include Orange 64 (CI 12760), one or more solvents, and one or more additives. The solvents may be *Hamamelis virginiana* Extract, ethyl alcohol, water, or any combination thereof. The solvents may be *Hamamelis virginiana* Extract, ethyl alcohol, and water. The additives may be selected from a group consisting of: an antifoaming agent (e.g., simethicone), a dispersant (e.g., ammonium acrylates copolymer), a binding agent, a humectant (e.g. glycerine), a wetting agent (e.g., alkyl polyglycoside), and any combination thereof. The orange pigment dispersion may include Orange 64 (CI 12760), one or more solvents, an antifoaming agent (e.g., simethicone), a dispersant (e.g., ammonium acrylates copolymer), a binding agent, a humectant (e.g. glycerine), and one or more additives. The orange pigment dispersion may include Orange 64 (CI 12760), *Hamamelis virginiana* Extract, ethyl alcohol, water, simethicone, ammonium acrylates copolymer, glycerine, polyethylene glycol, alkyl polyglycoside, and, optionally, one or more additives. The orange pigment dispersion may include Orange 64 (CI 12760), *Hamamelis virginiana* Extract, ethyl alcohol, water, simethicone, ammonium acrylates copolymer, glycerine, polyethylene glycol, D-Glucopyranose, oligomers, decyl octyl glycosides, and D-Glucopyranose, oligomeric, C10-16-alkyl glycosides. The orange pigment dispersion may have a viscosity of about 50 cP to about 200 cP as measured using any standard viscometer, which may also be referred to as a viscosity meter or rheometer, e.g., Viscolite 700 portable viscometer.

The pigment dispersion, or magenta pigment dispersion, may include Red 202 (CI 73907), one or more solvents, and one or more additives. The solvents may be *Hamamelis virginiana* Extract, ethyl alcohol, water, or any combination thereof. The solvents may be *Hamamelis virginiana* Extract, ethyl alcohol, and water. The additives may be selected from a group consisting of: an antifoaming agent (e.g., simethicone), a dispersant (e.g., ammonium acrylates copolymer), a binding agent, a humectant (e.g. glycerine), a wetting agent (e.g., alkyl polyglycoside), and any combination thereof. The magenta pigment dispersion may include Red 202 (CI 73907), one or more solvents, an antifoaming agent (e.g., simethicone), a dispersant (e.g., ammonium acrylates copolymer), a humectant (e.g. glycerine), and one or more additives. The magenta pigment dispersion may include Red 202 (CI 73907), *Hamamelis virginiana* Extract, ethyl alcohol, water, simethicone, ammonium acrylates copolymer, glycerine, polyethylene glycol, alkyl polyglycoside, and, optionally, one or more additives. The magenta pigment dispersion may include Red 202 (CI 73907), *Hamamelis virginiana* Extract, ethyl alcohol, water, simethicone, ammonium acrylates copolymer, glycerine, polyethylene glycol, D-Glucopyranose, oligomers, decyl octyl glycosides, and D-Glucopyranose, oligomeric, C10-16-alkyl glycosides. The magenta pigment dispersion may have a viscosity of about 50 cP to about 200 cP as measured using any standard viscometer, which may also be referred to as a viscosity meter or rheometer, e.g., Viscolite 700 portable viscometer.

The pigment dispersion, or red pigment dispersion, may include Red 254 (CI 56110), one or more solvents, and one or more additives. The solvents may be *Hamamelis virginiana* Extract, ethyl alcohol, water, or any combination thereof. The solvents may be *Hamamelis virginiana* Extract, ethyl alcohol, and water. The additives may be selected from a group consisting of: an antifoaming agent (e.g., simethicone), a dispersant (e.g., ammonium acrylates copolymer), a binding agent, a humectant (e.g. glycerine), a wetting agent (e.g., alkyl polyglycoside), and any combination thereof. The red pigment dispersion may include Red 254 (CI 56110), one or more solvents, an antifoaming agent (e.g., simethicone), a dispersant (e.g., ammonium acrylates copolymer), a humectant (e.g. glycerine), and one or more additives. The red pigment dispersion may include Red 254 (CI 56110), *Hamamelis virginiana* Extract, ethyl alcohol, water, simethicone, ammonium acrylates copolymer, glycerine, polyethylene glycol, alkyl polyglycoside, and, optionally, one or more additional additives. The red pigment dispersion may include Red 254 (CI 56110), *Hamamelis virginiana* Extract, ethyl alcohol, water, simethicone, ammonium acrylates copolymer, glycerine, polyethylene glycol, D-Glucopyranose, oligomers, decyl octyl glycosides, and D-Glucopyranose, oligomeric, C10-16-alkyl glycosides. The red pigment dispersion may have a viscosity of about 5 cP to about 50 cP as measured using any standard viscometer, which may also be referred to as a viscosity meter or rheometer, e.g., Viscolite 700 portable viscometer.

The pigment dispersion, or yellow pigment dispersion, may include Yellow 151 (CI 13980), one or more solvents, and one or more additives. The solvents may be *Hamamelis virginiana* Extract, ethyl alcohol, water, or any combination thereof. The solvents may be *Hamamelis virginiana* Extract, ethyl alcohol, and water. The additives may be selected from a group consisting of: an antifoaming agent (e.g., simethicone), a dispersant (e.g., ammonium acrylates copolymer), a binding agent, a humectant (e.g. glycerine), a wetting agent (e.g., alkyl polyglycoside), and any combination thereof. The yellow pigment dispersion may include Yellow 151 (CI 13980), one or more solvents, an antifoaming agent (e.g., simethicone), a dispersant (e.g., ammonium acrylates copolymer), a humectant (e.g. glycerine), and one or more additives. The yellow pigment dispersion may include Yellow 151 (CI 13980), *Hamamelis virginiana* Extract, ethyl alcohol, water, simethicone, ammonium acrylates copolymer, glycerine, polyethylene glycol, alkyl polyglycoside, and, optionally, one or more additives. The yellow pigment dispersion may include Yellow 151 (CI 13980), *Hamamelis virginiana* Extract, ethyl alcohol, water, simethicone, ammonium acrylates copolymer, glycerine, polyethylene glycol, D-Glucopyranose, oligomers, decyl octyl glycosides, and D-Glucopyranose, oligomeric, C10-16-alkyl glycosides. The Yellow 151 pigment dispersion may have a viscosity of about 10 cP to about 100 cP as measured using any standard viscometer, which may also be referred to as a viscosity meter or rheometer, e.g., Viscolite 700 portable viscometer.

The pigment dispersion, or yellow pigment dispersion, may include Yellow 180 (CI 21290), one or more solvents, and one or more additives. The solvents may be *Hamamelis virginiana* Extract, ethyl alcohol, water, or any combination thereof. The solvents may be *Hamamelis virginiana* Extract, ethyl alcohol, and water. The additives may be selected from a group consisting of: an antifoaming agent (e.g., simethicone), a dispersant (e.g., ammonium acrylates copolymer), a binding agent, a humectant (e.g. glycerine), a wetting agent (e.g., alkyl polyglycoside), and any combination thereof. The yellow pigment dispersion may include Yellow 180 (CI 21290), one or more solvents, an antifoaming agent (e.g., simethicone), a dispersant (e.g., ammonium acrylates copolymer), a binding agent, a humectant (e.g. glycerine), and one or more additives. The yellow pigment dispersion may include Yellow 180 (CI 21290), *Hamamelis virginiana* Extract, ethyl alcohol, water, simethicone, ammonium acrylates copolymer, glycerine, polyethylene glycol, alkyl polyglycoside, and, optionally, one or more additives. The yellow pigment dispersion may include Yellow 180 (CI 21290), *Hamamelis virginiana* Extract, ethyl alcohol, water, simethicone, ammonium acrylates copolymer, glycerine, polyethylene glycol, D-Glucopyranose, oligomers, decyl octyl glycosides, and D-Glucopyranose, oligomeric, C10-16-alkyl glycosides. The Yellow 180 pigment dispersion may have a viscosity of about 50 cP to about 200 cP as measured using any standard viscometer, which may also be referred to as a viscosity meter or rheometer, e.g., Viscolite 700 portable viscometer.

The pigment dispersion may comprise pigment in about 20 wt. % to about 60 wt. %, about 20% to about 50%, about 20 wt. % to about 40 wt. %, about 20 wt. % to about 30 wt. %, about 30 wt. % to about 40 wt. %, about 30 wt. % to about 60 wt. %, about 20 wt. % to about 25 wt. %, or about 25 wt. % to about 30 wt. % of the total pigment dispersion. The pigment dispersion may comprise water in about 20 wt. % to about 50 wt. %, about 20 wt. % to about 40 wt. %, about 30 wt. % to about 40 wt. %, about 20 wt. % to about 30 wt. %, or about 25 wt. % to about 30 wt. % of the total pigment dispersion. The pigment dispersion may comprise *Hamamelis virginiana* Extract in about 10 wt. % to about 25 wt. %, about 10 wt. % to about 15 wt. %, about 15 wt. % to about 20 wt. %, about 10 wt. % to about 20 wt. %, or about 20 wt. % to about 25 wt. % of the total pigment dispersion. The pigment dispersion may comprise ammonium acrylates copolymer in about 1 wt. % to about 20 wt. %, about 1 wt. % to about 10 wt. %, about 1 wt. % to about 5 wt. %, about 1 wt. % to about 3 wt. %, or about 2 wt. % to about 4 wt. % of the total pigment dispersion. The pigment dispersion may comprise glycerine in about 1 wt. % to about 5 wt. %, about 3 wt. % to about 5 wt. %, about 1 wt. % to about 3 wt. %, or about 2 wt. % to about 4 wt. % of the total pigment dispersion. The pigment dispersion may comprise propylene glycol in about 1 wt. % to about 5 wt. %, about 3 wt. % to about 5 wt. %, about 1 wt. % to about 3 wt. %, or about 2 wt. % to about 4 wt. % of the total pigment dispersion. The pigment dispersion may comprise ethyl alcohol in about 1 wt. % to about 5 wt. %, about 3 wt. % to about 5 wt. %, about 1 wt. % to about 3 wt. %, or about 2 wt. % to about 4 wt. % of the total pigment dispersion. The pigment dispersion may comprise alkyl polyglycosides in about 1 wt. % to about 15 wt. %, about 3 wt. % to about 10 wt. %, or about 5 wt. % to about 10 wt. % of the total pigment dispersion. The pigment dispersion may comprise D-Glucopyranose, oligomers, decyl octyl glycosides in about 1 wt. % to about 5 wt. %, about 3 wt. % to about 5 wt. %, about 1 wt. % to about 3 wt. %, or about 2 wt. % to about 4 wt. % of the total pigment dispersion. The pigment dispersion may comprise D-Glucopyranose, oligomeric, C10-16-alkyl glycosides in about 1 wt. % to about 5 wt. %, about 3 wt. % to about 5 wt. %, about 1 wt. % to about 3 wt. %, or about 2 wt. % to about 4 wt. % of the total pigment dispersion. The pigment dispersion may comprise simethicone in about 0.05 wt. % to about 1 wt. %, about 0.1 wt. % to about 0.9 wt. %, about 0.5 wt. % to about 0.8 wt. %, or about 0.3 wt. % to about 0.9 wt. % of the total pigment dispersion.

The range of particle size in the pigment dispersion may be about 150 nm to about 15 μm, about 150 nm to about 10 μm, about 150 nm to about 3 μm, about 85 nm to about 15 μm, about 85 nm to about 3 μm, about 70 nm to about 15 μm, about 70 nm to about 10 μm, about 70 nm to about 3 μm, about 60 nm to about 2 μm, about 50 nm to about 10 μm, or about 50 nm to about 3 μm. Particle size distributions may be measured using any device and method known for this use in the art. For example, particle size may be measured using Microtrac, SYNC 3R L, FLOW SYNC (wet analysis), by Laser Diffraction, and optionally, in particular: Laser Diffraction ISO 13320:2020.

The particle size distribution D90 (90 vol. %) of the pigment dispersion may be less than about 6 μm, less than about 3 μm, less than about 700 nm, less than about 650 nm, less than about 600 nm, less than about 500 nm, less than about 450 nm, less than about 400 nm, less than about 300 nm, or less than about 200 nm. The particle size distribution D90 (90 vol. %) of the pigment dispersion may be about 100 nm to about 6 μm, about 200 nm to about 3 μm, about 200 nm to about 1 μm, about 400 nm to about 900 nm, about 200 nm to about 700 nm, about 200 nm to about 500 nm, about 200 nm to about 400 nm, or about 250 nm to about 300 nm. Particle size influences toxicity, systemic exposure and ink performance. The particle size distributions for any pigment will consist of multiple size populations. Over about 50% of the particles may be in the micron range, and may be about 0.5 μm to about 1 μm, about 1 μm to about 2 μm, about 2 μm to about 3 μm, or about 3 μm to about 4 μm, or about 4 to about 5 μm. The pigment dispersion may contain one or more particle populations in the nanoparticle range. The pigment dispersion may contain less than about 1 vol. % to about 5 vol. %, about 1 vol. % to about 3 vol. %, or about 2 vol. % to about 3 vol. % in the nanoparticle range (1 nm-100 nm). The pigment dispersion may contain less than about 1 vol. %, about 1 vol. %, about 2 vol. %, about 3 vol. %, about 4 vol. %, or about 5 vol. %, in the nanoparticle range (1 nm-100 nm). Table 1 presents certain parameters of particle sizes for pigment dispersions containing different pigments.

TABLE 1

| Pigment Dispersion containing the listed pigment | Particle size range | D90 | Volume % of nanoparticles |
| --- | --- | --- | --- |
| Carbon Black | about 85 nm-about 15 μm | <about 3 μm | About 3 vol % of particles are in the nanoparticle range (1-100 nm) |
| Blue 15 | about 85 nm-about 3 μm | <about 600 μm | About 2 vol % of particles are in the nanoparticle range (1-100 nm). |
| Blue 16 | about 60 nm-about 10 μm | <about 5 μm | About 5 vol % of particles are in the nanoparticle range (1-100 nm). |
| Blue 60 | about 60 nm-about 15 μm | <about 5 μm | About 5 vol % of particles are in the nanoparticle range (1-100 nm). |
| Green 7 | about 60 nm-about 10 μm | <about 5 μm | About 5 vol % of particles are in the nanoparticle range (1-100 nm). |
| Green 36 | about 60 nm-about 10 μm | <about 5 μm | About 5 vol % of particles are in the nanoparticle range (1-100 nm). |
| Orange 64 | about 60 nm-about 2 μm | <about 500 μm | About 3 vol % of particles are in the nanoparticle range (1-100 nm). |
| Red 202 | about 150 nm-about 30 μm | <about 6 μm | Less than 1 vol % of particles are in the nanoparticle range (1-100 nm). |

TABLE 1-continued

| Pigment Dispersion containing the listed pigment | Particle size range | D90 | Volume % of nanoparticles |
|---|---|---|---|
| Red 254 | about 50 nm-about 2 µm | <about 450 µm | About 5 vol % of particles are in the nanoparticle range (1-100 nm). |
| TiO$_2$ | about 65 nm-about 1 µm | <about 500 µm | About 2 vol % of particles are in the nanoparticle range (1-100 nm). |
| Yellow 151 | about 70 nm-about 3 µm | <about 650 µm | About 2 vol % of particles are in the nanoparticle range (1-100 nm). |
| Yellow 180 | about 50 nm-about 10 µm | <about 650 µm | Approximately 3 vol % of particles are in the nanoparticle range (1-100 nm). |

The pigment dispersions disclosed herein have reduced impurity content by the use of carefully developed processing procedures. Raw material vendors should adhere to consistent quality management systems and practices to ensure constancy in the product (e.g., guidelines from ISO 9001). ISO is the International Organization for Standardization that provides specific requirements covering quality and safety aspects of all raw materials as well as finished goods. The pigment dispersions may meet the purity requirements set out by the COMMISSION REGULATION (EU) 2020/2081 ("EU Regulation"). According to the EU Regulation, pigment dispersions must not contain the following impurities above the stated limits:

1. Free primary aromatic amines (PAA) according to Annex XVII to Regulation (EC) No. 1907/2006 (Reach); limit 5 ppm per PAA
2. Heavy metals according to appendix 13 of Annex XVII to Regulation (EC) No. 1907/2006; limit for each heavy metal species is specified in referenced regulation.
3. Polycyclic aromatic hydrocarbons (PAH); limit 0.5 ppm per PAH compound, 5 ppb for Benzo[a]pyrene
4. Methanol; limit 11% by weight
5. Dyes, pigments, and colorants listed in Appendix 13 of Annex XVII to Regulation (EC) No. 1907/2006; Limit 0.1%
6. Preservatives, phthalates, and other substances with the following hazardous classification according to Part 3 of Annex VI to Regulation (EC) No 1272/2008
   a. Carcinogen category 1A, 1B, or 2, or germ cell mutagen category 1A, 1B or 2; limit 0.00005% by weight
   b. Reproductive toxicant category 1A, 1B or 2; limit 0.001% by weight
   c. Skin sensitizer category 1, 1A or 1B; limit 0.001% by weight
   d. Skin corrosive category 1, 1A, 1B or 1C, or skin irritant category 2, or as serious eye damage category 1 or eye irritant category 2; limit 0.1% by weight if used solely as a pH regulator, limit 0.01% by weight in all other cases.
7. Substances listed in Annex II to Regulation (EC) No 1223/2009 of the European Parliament and of the Council
   a. Limit 0.0005% by weight
8. Substances listed in Annex IV to Regulation (EC) No 1223/2009 for which any of the following conditions is specified in at least one of the columns, g, h, and I of the table in that Annex
   a. "Rinse-off products"; limit 0.00005% by weight
   b. "Not to be used in products applied on mucous membranes"; limit 0.00005% by weight
   c. "Not to be used in eye products"; limit 0.00005% by weight The pigment dispersion may include impurities in less than or equal to about 0.5 ppm total polycyclic aromatic hydrocarbons; less than about 5 ppb benzo[a]pyrene (BaP); less than 5 ppm primary aromatic amines; and/or less than 11 wt. % methanol.

Table 2 shows examples of acceptable limits for the presence of certain metals is pigment dispersions disclosed herein. The pigment dispersion may have less than each of the limits for each of the metals listed in Table 2. The pigment dispersion may contain less than about 0.5 ppm of impurities selected from the group consisting of: mercury, organometallic tin, antimony, arsenic, cadmium, chromium (Cr(VI)), or any combination thereof. The pigment dispersion may contain less than about 0.7 ppm of lead. The pigment dispersion may contain less than about 5 ppm of nickel. The pigment dispersion may contain less than about 500 ppm of barium. The pigment dispersion may contain less than about 250 ppm of copper. The pigment dispersion may contain less than about 2 ppm of selenium. The pigment dispersion may contain less than about 2000 ppm of zinc.

TABLE 2

| Metal | Limit |
|---|---|
| Mercury | 0.5 ppm |
| Nickel | 5 ppm |
| Organometallic tin | 0.5 ppm |
| Antimony | 0.5 ppm |
| Arsenic | 0.5 ppm |
| Barium (soluble)** | 500 ppm |
| Cadmium | 0.5 ppm |
| Chromium as Cr (VI) | 0.5 ppm |
| Cobalt | 0.5 ppm |
| Copper (soluble)** | 250 ppm |
| Zinc (soluble)** | 2000 ppm |
| Lead | 0.7 ppm |
| Selenium | 2 ppm |

The pigment dispersion disclosed herein may have less than 0.5 ppm of one or more of the polyaromatic hydrocarbons listed in Table 3. The pigment dispersion disclosed herein may have less than 0.005 ppm (5 ppb) of Benz[a]pyrene. The pigment dispersion disclosed herein may have less than 0.005 ppm (5 ppb) of Benz[a]pyrene and less than 0.5 ppm of one or more of the polyaromatic hydrocarbons listed in Table 3.

TABLE 3

Polyaromatic hydrocarbons
Method: AFPS GS 2019:01 PAK, extraction in toluene
Limit: 0.5 ppm
Limit of quantitation: 0.5 ppm

| | | |
|---|---|---|
| Naphthalene | Acenaphthalene | Acenaphthene |
| Fluorene | Phenanthrene | Anthracene |
| Fluoranthene | Pyrene | Benzo[a]anthracene |
| Chrysene | Benzo[b]fluoranthene | Benzo[k]fluoranthene |
| Benzo[ghi]perylene | Dibenzo[ah]anthracene | Indeno[1,2,3,cd]pyrene |
| Cyclopenta[cd]pyrene | Benzo[i]fluoranthene | Benzo[e]pyrene |
| Dibenzo[ai]pyrene | Dibenzo[a]pyrene | Dibenzo[ae]pyrene |
| Benzo[c]fluorene | Dibenzo[ah]pyrene | 1-Methylpyrene |
| | 5-Methylchrysene | |

The pigment dispersion disclosed herein may contain less than about 5 ppm of free aromatic amines listed in Table 4, which is a list according to Regulation 1907/2006 Annex XVII (Reach) of the European Parliament and the Council Method. For the compounds in Table 4, extraction with MeOH, and analysis with GC/MS.

TABLE 4

Free Aromatic Amines

| | |
|---|---|
| 4-Aminobiphenyl** | Benzidine** |
| 4-Chloro-o-toluidine** | 2-Naphtylamine** |
| 4-o-Tolylazo-o-toluidin** | 5-Nitro-o-toluidine** |
| 4-Chloroaniline** | 4-Methoxy-m-phenylendiamine** |
| 4,4'-Methylenedianiline** | 3,3'-Dichlorobenzidine** |
| 3,3'-Dimethoxybenzidine** | 4,4'-Bi-o-Toluidin** |
| 4,4'-Methylenedi-o-toluidine** | 6-Methoxy-m-toluidine** |
| 4,4'-Methylenebis-(2-chloroaniline)** | 4-Methyl-m-phenylendiamine** |
| o-Anisidine** | 4-Aminoazobenzene** |
| 2-Methyl-p-phenylendiamin** | 4-Amino-3-florophenol** |
| 4,4'-Oxydianilinie** | 4,4'-Thiodianiline** |
| o-Toluidine** | 2,4,5-Trimethylaniline** |
| p-Phenylendiamine** | Aniline** |
| p-Toluidine** | Sulfanilic acid** |
| 2,6-Xylidine | 6-Amino-2-ethoxynaphtaline |
| 2,4-Xylidine | |

**soluble

A tattoo ink formulation is disclosed that includes any pigment dispersion disclosed herein. The tattoo ink formulation may include: a pigment dispersion comprising: $TiO_2$ (CI 77891), Blue15 (CI 74160), Carbon black (CI 77266), Orange 64 (CI 12760), Red 202 (CI 73907), Red 254 (CI 56110), Yellow 151 (CI 13980), Yellow 180 (CI 21290), Blue 16 (CI 74100), Blue 60 (CI 69800), Green 36 (CI 74265), Green 7 (CI 74260), or any combination thereof; a solvent; and at least one additive. The tattoo ink formulation may comprise less than about 95 wt. %, about 1 wt. % to about 95%, or about 10 wt. % to about 95% of the pigment dispersion.

The tattoo ink formulation may comprise a pigment dispersion comprising: $TiO_2$ (CI 77891), Blue15 (CI 74160), Carbon black (CI 77266), Orange 64 (CI 12760), Red 202 (CI 73907), Red 254 (CI 56110), Yellow 151 (CI 13980), Yellow 180 (CI 21290), Blue 16 (CI 74100), Blue 60 (CI 69800), Green 36 (CI 74265), Green 7 (CI 74260), or any combination thereof; a solvent selected from the group consisting of water, ethyl alcohol, *Hamamelis virginiana* Extract, and a combination thereof; and glycerine. The tattoo ink formulation may comprise any pigment dispersion disclosed herein. The tattoo ink formulation may contain *Hamamelis virginiana* Extract in about 1 wt. % to about 50 wt. %, about 10 wt. % to about 40 wt. %, about 1 wt. % to about 30 wt. %, or about 20 wt. % to about 40 wt. %, of the total tattoo ink formulation. The tattoo ink formulation may contain water in about 1 wt. % to about 50 wt. %, about 10 wt. % to about 40 wt. %, about 1 wt. % to about 30 wt. %, or about 20 wt. % to about 40 wt. %, of the total tattoo ink formulation. The tattoo ink formulation may contain glycerine in about 1 wt. % to about 40 wt. %, about 10 wt. % to about 40 wt. %, about 1 wt. % to about 30 wt. %, about 10 wt. % to about 20 wt. %, or about 20 wt. % to about 40 wt. %, of the total tattoo ink formulation. The tattoo ink formulation may contain ethyl alcohol in about 0.1 wt. % to about 5 wt. %, about 1 wt. % to about 5 wt. %, about 0.5 wt. % to about 3 wt. %, or about 0.1 wt. % to about 2 wt. %, of the total tattoo ink formulation. The tattoo ink formulation may have a viscosity of less than about 500 cP, about 50 cP to about 500 cP, or about 2000 cP to about 500 cP, as measured using any standard viscometer, which may also be referred to as a viscosity meter or rheometer, e.g., Viscolite 700 portable viscometer.

The tattoo ink formulation disclosed herein may contain less than about 5%, less than about 4%, less than about 3%, less than about 2%, less than about 1% by weight of impurities. The tattoo ink formulation disclosed herein may contain less than about 5 ppm of free aromatic amines listed in Table 4.

The tattoo ink formulation may contain less than or equal to about 0.5 ppm total polycyclic aromatic hydrocarbons. The tattoo ink formulation may contain: less than or equal to about 5 ppm of free aromatic amines listed in Table 4; less than or equal to about 11 wt % of methanol; less than or equal to about 0.1 wt % of dyes, pigments, and colorants listed in Table 5 and listed in COMMISSION REGULATION (EU) 2020/208; less than or equal to about 0.5 ppm carcinogens category 1A, 1B, or 2, or germ cell mutagens category 1A, 1B, or 2 according to Part 3 of Annex VI to Regulation (EC) No 1272/2008 (http://data.europa.eu/eli/reg/2008/1272/2022-03-01); less than or equal to about 10 ppm reproductive toxicants category 1A, 1B, or 2, or skin sensitizers category 1, 1A, or 1B according to Part 3 of Annex VI to Regulation (EC) No 1272/2008 (http://data.europa.eu/eli/reg/2008/1272/2022-03-01); less than or equal to about 100 ppm skin corrosives category 1, 1A, 1B or 1C, or skin irritants category 2, or serious eye damage category 1, or eye irritant category 2 according to Part 3 of Annex VI to Regulation (EC) No 1272/2008 (http://data.europa.eu/eli/reg/2008/1272/2022-03-01); less than or equal to about 5 ppm substances listed in Annex II to Regulation (EC) No 1223/2009 (http://data.europa.eu/eli/reg/2009/1223/2022-10-06); less than or equal to about 0.5 ppm of substances listed in Annex IV of Regulation (EC) No 1223/2009 (http://data.europa.eu/eli/reg/2009/1223/2022-10-06) for which the following categories apply: "Rise-off products", "Not to be used in products applied on mucous membranes", "not to be used in eye products."

TABLE 5

Dyes, pigments, and colorants listed in COMMISSION REGULATION (EU)
2020/2081 (limit is 0.1 wt % or 1000 ppm)

| | |
|---|---|
| Pigment Red 7 (PR7)/CI 12420 | Pigment Orange 13 (PO13)/CI 21110 |
| Pigment Red 9 (PR9)/CI 12460 | Pigment Orange 34 (PO34)/CI 21115 |
| Pigment Red 15 (PR15)/CI 12465 | Pigment Yellow 83 (PY83)/CI 21108 |
| Pigment Red 210 (PR210)/CI 12477 | Solvent Red 1 (SR1)/CI 12150 |

TABLE 5-continued

Dyes, pigments, and colorants listed in COMMISSION REGULATION (EU) 2020/2081 (limit is 0.1 wt % or 1000 ppm)

| | |
|---|---|
| Pigment Orange 74 (PO74) | Acid Orange 24 (AO24)/CI 20170 |
| Pigment Yellow 65 (PY65)/CI 11740 | Solvent Red 23 (SR23)/CI 26100 |
| Pigment Yellow 74 (PY74)/CI 11741 | Acid Red 73 (AR73)/CI 27290 |
| Pigment Red 12 (PR12)/CI 12385 | Disperse Yellow 3/CI 11855 |
| Pigment Red 14 (PR14)/CI 12380 | Acid Green 16/CI 44025 |
| Pigment Red 17 (PR17)/CI 12390 | Acid Red 26/CI 18050 |
| Pigment Red 112 (PR112)/CI 12370 | Acid Violet 17/CI 42650 |
| Pigment Yellow 14 (PY14)/CI 21095 | Basic Red 1/CI 45160 |
| Pigment Yellow 55 (PY55)/CI 21096 | Disperse Blue 106/CI 111935 |
| Pigment Red 2 (PR2)/CI 12310 | Disperse Blue 124/CI 111938 |
| Pigment Red 22 (PR22)/CI 12315 | Disperse Blue 35/CI 636010 |
| Pigment Red 146 (PR146)/CI 12485 | Disperse Orange 37/CI 11132 |
| Pigment Red 269 (PR269)/CI 12466 | Disperse Red 1/CI 11110 |
| Pigment Orange 16 (PO16)/CI 21160 | Disperse Red 17/CI 11210 |
| Pigment Yellow 1 (PY1)/CI 11680 | Disperse Yellow 9/CI 10375 |
| Pigment Yellow 12 (PY12)/CI 21090 | Pigment Violet 3/CI 42535 |
| Pigment Yellow 87 (PY87)/CI 21107:1 | Pigment Violet 39/CI 42555 |
| Pigment Yellow 97 (PY97)/CI 11767 | Solvent Yellow 2/CI 11020 |

The tattoo ink formulation may have a weight loss on heating for about 950° C. for about 7 minutes to be about 0% to about 4% by weight.

The tattoo ink formulation disclosed herein may be formulated without tea, mineral oil, petroleum, or without any of the foregoing. The pigment dispersions disclosed herein may be formulated without tea, mineral oil, petroleum, or without any of the foregoing.

Also disclosed are processes for making the pigment dispersions disclosed herein. Pigment dispersions (also referred to as base colors) may best be manufactured in a controlled environment. Manufacturing facilities may be certified under ISO 22716:2007 and ISO 9001:2015 for Cosmetic Products, and under ISO 13485:2016 for Medical devices, or any similar or updated versions of these standards. Pigment dispersions may be batch monitored for consistency by recording viscosity (Viscolite VL700 d21 or similar instrument) and spectral properties (using a spectrophotometer).

The method of making a pigment dispersion may include mixing the pigment with the other ingredients using a high shear mixer, which may also be referred to as a high shear reactor, rotor-stator mixer, or high shear homogenizer. The functional component of a high shear mixer, known as mixer head or generator, generates shear force that disperses the pigment. The mixer head may include a rotatable rotor or impeller, and a stationary stator. The amount of shear force exerted on the mixture may be adjusted by changing the speed of the rotor. The speed of the rotatable rotor may be about 1,000 feet per minute (FPM) to about 20,000 FPM, about 2,000 FPM to about 10,000 FPM, about 2,000 FPM to about 5,000 FPM, about 5,000 FPM to about 10,000 FPM, or about 10,000 FPM to about 20,000 FPM. The short distance between the rotatable rotor and stationary stator creates an ultra-high shear zone, with shear rates ranging anywhere from about 20,000 $s^{-1}$ to about 100,000 $s^{-1}$. The stationary stator may have a stator head comprising openings. The openings on the stator head may be adjustable. The stator head openings may be round, square, slotted or fine screen. The mixer head may include multiple layers of rotating and stationary components, making up an array of rotor/stators. As the undispersed liquid/solid is drawn into the rotator/stator axially and expelled radially through the openings on the stator head, the pigment becomes dispersed.

A variety of different high shear mixer configurations may be used to disperse pigments in accordance with this disclosure. These include Batch High Shear Mixers, In-line High Shear Mixers, and Powder Induction High Shear Mixers. The total mixing time may be about 1 hour to about 5 hours, about 1 hour to about 4 hours or about 2 hours to about 4 hours.

With Batch High Shear Mixers, all the ingredients are added from the top of a single tank or vessel. The mixer head may be located on a rotating shaft at the bottom of the tank, or the mixing head may be suspended in the tank allowing for adjustment of mixer head height. The order of additions can be liquids followed by pigment powder, or powder followed by liquid ingredients, or concurrent addition of both liquid ingredients and pigment powder. The shear force applied to the mixture can be set by adjusting the revolutions per minute (RPM) of the rotor. The rotor speed may be about 1,000 RPM to about 2,000 RPM, about 2,000 RPM to about 4,000 RPM, or about 4,000 RPM to about 10,000 RPM. The rotor speed can be kept constant or increased stepwise throughout the dispersing process. The mixture temperature may be maintained at ambient room temperature, e.g., about 68° F. to about 77° F. (about 20° C. to about 25° C.), or it may be warmed up to about 110° F. (about 43° C.), such that the temperature range is about 68° F. to about 110° F. (about 20° C. to about 43° C.). The mixing may continue until the solution becomes homogenous. Homogeneity may be checked by qualitative method of ink spreading onto a flat surface and observing any aggregates.

With In-Line High Shear Mixers, the shear mixer is contained in an external chamber with an inlet and outlet tubing that feed back into the main reservoirs. The shear force applied to the mixture may be set by adjusting the revolutions per minute (RPM) of the rotor. The rotor speed may be about 1,000 RPM to about 2,000 RPM, about 2,000 RPM to about 4,000 RPM, or about 4,000 RPM to about 10,000 RPM. The rotor speed can be kept constant or increased stepwise throughout the dispersing process. The mixture flow rate may also be adjusted and typically runs from about 5 to about 50,000 gallons per hour The mixture temperature may be maintained at ambient room temperature, e.g., about 68° F. to about 77° F. (about 20° C. to about 25° C.), or it may be warmed up to about 110° F. (about 43° C.), such that the temperature range is about 68° F. to about 110° F. (about 20° C. to about 43° C.). The mixing may continue until the solution becomes homogenous. Homogeneity may be checked by qualitative method of ink spreading onto a flat surface and observing any aggregates. The in-line high shear mixer may reduce the dispersion time and provide more controlled particle size reduction. In-line mixing is done in a continuous stream, which may allow for more efficient wetting and stabilization of pigment particles. It also prevents clumping, which can hinder the efficiency of dispersion in batch high shear mixing.

With Powder Induction High Shear Mixers, a vacuum system is used to draw powder ingredients directly into the mixing head. At the same time, liquids are circulated through the mixing head by an accompanying pipe/line. This allows a more controlled addition of powder ingredients into the dispersion process. The liquid recirculating line speed may also be adjusted and typically runs from about 5 to about 50,000 gallons per hour. The shear force applied to the mixture may be set by adjusting the revolutions per minute (RPM) of the rotor. The rotor speed may be about 1,000 RPM to about 2,000 RPM, about 2,000 RPM to about 4,000 RPM, or about 4,000 RPM to about 10,000 RPM. The rotor speed can be kept constant or increased stepwise throughout the dispersing process. The mixture temperature may be maintained at ambient room temperature, e.g., about 68° F. to about 77° F. (about 20° C. to about 25° C.), or it may be warmed up to about 110° F. (about 43° C.), such that the temperature range is about 68° F. to about 110° F. (about 20° C. to about 43° C.). The mixing may continue until the solution becomes homogenous. Homogeneity may be checked by qualitative method of ink spreading onto a flat surface and observing any aggregates.

Pigment dispersion comprising Blue 60 pigment may achieve improved results with respect to complete particle size reduction by use of an in-line high sheer mixer instead of the batch high shear mixer. Alternatively, the liquid mixture may first be passed through a media mill (or other similarly functioning apparatus known in the art) and then subjected to mixing in a batch high shear mixer.

A method of making a pigment dispersion is disclosed including combining the following ingredients: at least one solvent selected from the group consisting of *Hamamelis virginiana* Extract, ethyl alcohol, water, or any combination thereof; simethicone; glycerine; a dispersant; and one or more additives, to make a solution, and then mixing the solution to make a homogenous mixture. The homogenous mixture is placed in a high shear mixer at about 2000 RPM to about 4000 RPM and a pigment is added. Mixing continues for about 1 hour to about 4 hours, about 2 hours to about 4 hours, or about 2 hours to about 3 hours, at a temperature of about 68° F. to about 110° F. to make a homogenous pigment dispersion.

A method of making a pigment dispersion with powder induction is disclosed including combining the following ingredients: at least one solvent selected from the group consisting of *Hamamelis virginiana* Extract, ethyl alcohol, water, or any combination thereof; simethicone; glycerine; a dispersant; and one or more additives, to make a solution, and then mixing the solution to make a homogenous mixture. The homogenous mixture is placed in an in-line high shear at about 3000 RPM to about 4000 RPM, about 3500 RPM to about 4000 RPM, or about 3600 RPM, while adding a pigment to the homogenous mixture through a powder induction system. The powder induction system, for example, ADMIX® Fastfeed® Powder Induction and Dispersion System, comprises a vacuum pump which may work at about 14" Hg. The vacuum pump suctions the powder into the in-line high shear mixture and also circulates the mixture within the in-line high shear mixer. The powder induction system may be coupled to the in-line high shear mixer by any means known in the art. Mixing continues for about 1 hour to about 4 hours, about 2 hours to about 4 hours, or about 2 hours to about 3 hours, at a temperature of about 68° F. to about 110° F. to make a homogenous pigment dispersion. Homogeneity may be confirmed by qualitative method of ink spreading onto a flat surface and observing any aggregates.

The method may also include cooling the in-line high shear mixer with water, optionally an external cooling bath, while mixing.

Base pigment dispersions are used to create final ready-to-use products. The process of making final ready-to-use products must be done in an ISO certified class 6 clean room. Quality control checks as established by ISO 22716:2007, ISO 9001:2015, and ISO 13485:2016 are used to guarantee batch to batch conformity. These include, but are not limited to, tattoo ink density, viscosity, UV-Vis Spectral properties, Color Strength, pH, Ingredient formulation, and sterility.

Final tattoo ink products should be void of any microbiological contamination, including the microbiological classes listed below. Limit of detection should be <10 colony forming units/gram (CFU/g).

Microbiological Classes to be Tested
1. Spores of aerobes spore-forming
2. Spores of anaerobes spore-forming
3. *Bacillus cereus* presumptive
4. Sulphite reducing clostridia
5. Total viable count, aerobes mesophil 30° C.
6. Total viable count, anaerobes mesophil 30° C.
7. *Pseudomonas* sp.

Final tattoo ink products must be sterilized prior to retail distribution. Sterilization may be accomplished by X-ray irradiation or gamma irradiation. The sterilization procedure may be validated by USP<71> or a similar method. Outsourced sterility facilities may have the following certifications: ISO 9001:2015, ISO 13485:2016, or both.

EXAMPLES

Example 1: Carbon Black Pigment Dispersion Process

Dispensing Liquids

Each dispersing ingredient (liquid) is measured by weight according to the master formula and transferred to recirculation tank. Turn on pump and in-line shear mixer to allow liquid to circulate through the system. Allow system to flood with liquid for 5 minutes minimum.

Adding Pigment Raw Powder

Prior to adding pigment powder, operator must don full body clean suit and face shield, including safety mask. After checking that liquid is circulating through system, add weighed powder to the hopper. Open cooling water valve and the powder valve to allow powder into the circulation line. Start the external tank mixer. Flow and Pressure should be calibrated to reach the recommended 0.3 to 0.5 gallons per minute with a minimum of 30 PSI pressure.

Mixing and Dispersion Process

Once all powder has been added, close the powder valve and restrict the shear valve. Allow liquid to shear mix for 2 hours.

Quality Control

Production Manager must record notes during powder dispersion process. After 2 hours, a sample is taken from the homogeneous dispersed and allowed to cool to room temperature. Quality Control measures the live viscosity reading using Hydromotion Viscolite 700 portable viscometer. Acceptable viscosity readings are 10-200 cP. Quality Control obtains drawdowns of the dispersion and compares CIE LAB values to established standard.

Stability Data

High Purity Furnace Black (Carbon Black) is known to be stable and inert. No chemical degradation is expected. Although no chemical degradation is expected, recent tattoo safety has focused on carbon black nanoparticle distribution and the ability to induce reactive oxygen species. Three batches of Black Base Color composition were manufactured, RMP004, RMP005, and RMP006. Stability Studies were conducted on these three batches.

Stability Study Condition 1: Samples were stored in controlled chambers at 25° C., 60% relative humidity.

TABLE 6

Summary of nanoparticle size distribution for lot RBP004 condition 1

Nanoparticle Distribution for RBP004 stored at at 25° C., 60% relative humidity (Intensity-Weighted Results)

| Time Point (month) | Z-average (nm) | PDI | Peak 1 and width (nm) | Peak 1 Intensity (%) | Peak 2 and width (nm) | Peak 2 Intensity | Peak 3 and width (nm) | Peak 3 Intensity (%) |
|---|---|---|---|---|---|---|---|---|
| 0 | 237.8 | 0.19 | 271.1 (126.6) | 98.6 | 4560 (1022) | 1.4 | N/A | N/A |
| 1 | 290.6 | 0.21 | 332.3 (128.1) | 98.5 | 5008 (637.9) | 1.5 | N/A | N/A |
| 2 | 246.8 | 0.29 | 247 (75.34) | 97.2 | 5032 (627.3) | 2.8 | N/A | N/A |

TABLE 7

Summary of nanoparticle size distribution for lot RBP005 condition 1

Nanoparticle Distribution for RBP005 stored at at 25° C., 60% relative humidity (Intensity-Weighted Results)

| Time Point (mo.) | Z-average (nm) | PDI | Peak 1 and width (nm) | Peak 1 Intensity (%) | Peak 2 and width (nm) | Peak 2 Intensity | Peak 3 and width (nm) | Peak 3 Intensity (%) |
|---|---|---|---|---|---|---|---|---|
| 0 | 243.4 | 0.16 | 266.6 (88.86) | 100 | N/A | N/A | N/A | N/A |
| 1 | 277.2 | 0.22 | 297.1 (124.8) | 97.7 | 4848 (807.0) | 2.3 | N/A | N/A |
| 2 | 261.6 | 0.33 | 248.3 (74.68) | 96.6 | 4966 (669.0) | 3.4 | N/A | N/A |

TABLE 8

Summary of nanoparticle size distribution for lot RBP006 condition 1

Nanoparticle Distribution for RBP006 stored at at 25° C., 60% relative humidity (Intensity-Weighted Results)

| Time Point (mo.) | Z-average (nm) | PDI | Peak 1 (and width) in nm | Peak 1 Intensity (%) | Peak 2 and width (nm) | Peak 2 Intensity | Peak 3 (and width) in nm | Peak 3 Intensity (%) |
|---|---|---|---|---|---|---|---|---|
| 0 | 265.5 | 0.22 | 293.0 (123.4) | 97.6 | 4330 (1174) | 2.3 | 61.14 (6.300) | 0.1 |
| 1 | 291.7 | 0.25 | 301.7 (116.3) | 97.1 | 4509 (898.7) | 2.9 | N/A | N/A |
| 2 | 327.3 | 0.45 | 393.2 (297.5) | 95.1 | 4753 (826.8) | 4.9 | N/A | N/A |

Stability Study Condition 2: Samples were stored in controlled chambers at 40° C., 75% relative humidity.

TABLE 9

Summary of nanoparticle size distribution for lot RBP004 condition 2

Nanoparticle Distribution for RBP004 stored at 40° C., 75% relative humidity
(Intensity-Weighted Results)

| Time Point (mo.) | Z-average | PDI | Peak 1 (and width) in nm | Peak 1 Intensity (%) | Peak 2 (and width) in nm | Peak 2 Intensity | Peak 3 (and width) in nm | Peak 3 Intensity (%) |
|---|---|---|---|---|---|---|---|---|
| 0 | 237.8 | 0.19 | 271.1 (126.6) | 98.6 | 4560 (1022) | 1.4 | N/A | N/A |
| 1 | 293.5 | 0.20 | 309.2 (106.9) | 98.6 | 4885 (747.1) | 1.4 | N/A | N/A |
| 2 | 255.8 | 0.24 | 265.8 (111.3) | 96.7 | 1669 (646.2) | 2.6 | 4935 (666.4) | 0.8 |

TABLE 10

Summary of nanoparticle size distribution for lot RBP005 condition 2

Nanoparticle Distribution for RBP005 stored at at 40° C., 75% relative humidity
(Intensity-Weighted Results)

| Time Point (mo.) | Z-average (nm) | PDI | Peak 1 (and width) in nm | Peak 1 Intensity (%) | Peak 2 (and width) in nm | Peak 2 Intensity | Peak 3 (and width) in nm | Peak 3 Intensity (%) |
|---|---|---|---|---|---|---|---|---|
| 0 | 243.4 | 0.16 | 266.6 (88.86) | 100 | N/A | N/A | N/A | N/A |
| 1 | 292.4 | 0.22 | 304.3 (110.2) | 96.4 | 4461 (869.4) | 3.6 | N/A | N/A |
| 2 | 239.7 | 0.25 | 259.3 (97.04) | 99.2 | 5104 (542.9) | 0.8 | N/A | N/A |

TABLE 11

Summary of nanoparticle size distribution for lot RBP006 condition 2

Nanoparticle Distribution for RBP006 stored at at 40° C., 75% relative humidity
(Intensity-Weighted Results)

| Time Point (mo.) | Z-average (nm) | PDI | Peak 1 (and width) in nm | Peak 1 Intensity (%) | Peak 2 (and width) in nm | Peak 2 Intensity | Peak 3 (and width) in nm | Peak 3 Intensity (%) |
|---|---|---|---|---|---|---|---|---|
| 0 | 265.5 | 0.22 | 293.0 (123.4) | 97.6 | 4330 (1174) | 2.3 | 61.14 (6.300) | 0.1 |
| 1 | 305.3 | 0.21 | 340.9 (139.3) | 98.8 | 5204 (471.9) | 1.1 | 64.90 (9.483) | 0.1 |
| 2 | 366.2 | 0.32 | 416.0 (202.5) | 97.3 | 4918 (663.1) | 2.7 | N/A | N/A |

Example 2: Formulations of Pigment Dispersions

Pigment dispersions of the formulations in Tables 12, 14, 16, 18, 20, 22 and 24 were made according to the following processing steps.

First, except for the pigment, the ingredients, including, as explicable per the formulation tables below, distilled water, solvents (e.g., *Hamamelis virginiana* Extract, Ethyl alcohol), dispersant (e.g. ammonium acrylates copolymer), wetting agents (e.g., alkyl polyglycosides), humectants (e.g., glycerine, propylene glycol), antifoaming agent (e.g. simethicone), are added to a mixing vessel at room temperature and stirred until homogeneous.

The color pigment in the form of a powder is then added to the homogeneous dispersing solution in parts. The resulting mixture is dispersed using an external high shear mixer at 2000-4000 RPM. The high shear mixing head speed is adjusted by the operator. The mixture solution temperature is kept between 68° F.-110° F. and mixed for 2-3 hrs, until the solution becomes homogenous. Homogeneity is checked by qualitative method of ink spreading onto a flat surface and observing any aggregates. The resulting homogenous mixture is a pigment dispersion that may be used to make a tattoo ink formulation.

Pigment Black 7
Pigment Identity: Carbon Black; Black 7; High Purity Furnace Black; CI 77266
Base Color Shade: Black

TABLE 12

Black 7 Pigment Dispersion Formulation

| Chemical | EC Number | CAS Number | Percentage |
|---|---|---|---|
| CI 77266 | 215-609-9 | 1333-86-4 | 20-40% |
| Distilled Water | 231-791-2 | 7732-18-5 | 20-40% |

TABLE 12-continued

Black 7 Pigment Dispersion Formulation

| Chemical | EC Number | CAS Number | Percentage |
| --- | --- | --- | --- |
| *Hamamelis Virginiana* Extract | 283-637-9 | 84696-19-5 | 10-25% |
| Ammonium Acrylates Copolymer | Not Registered | 63744-68-3 | 1-5% |
| Glycerine | 200-289-5 | 56-81-5 | 1-5% |
| Propylene Glycol | 200-338-0 | 57-55-6 | 1-5% |
| Ethyl Alcohol | 200-578-6 | 64-17-5 | 1-5% |
| D-Glucopyranose, oligomeric, C10-16-alkyl glycosides | 600-975-8 | 110615-47-9 | 1-5% |
| D-Glucopyranose, oligomers, decyl octyl glycosides | 500-220-1 | 68515-73-1 | 1-5% |
| Simethicone | 617-098-1 | 8050-81-5 | <1% |

Figure 2:
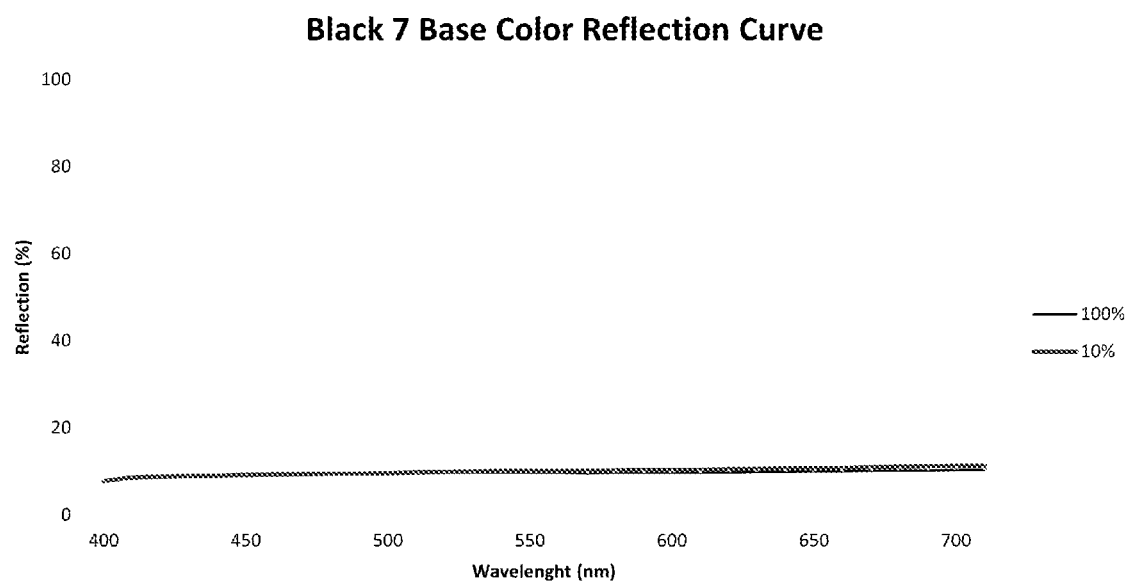
FIG. 2 is a graph of the color reflection curve for a pigment dispersion containing Black 7.

The Black 7 pigment dispersion processed by the method above has a reflection curve shown in FIG. 2 and CIE LAB values as shown in Table 13. The term "base color" as used in the figures refers to the pigment dispersion.

TABLE 13

Black 7 Base Color CIE LAB Values

| Ink Concentration (wt/wt) | L* | a* | b* | C* | h* |
| --- | --- | --- | --- | --- | --- |
| 100% | 32.96 | 0.23 | 2.06 | 2.07 | 83.64 |
| 10%¥ | 29.41 | 1.20 | 5.22 | 5.36 | 77.09 |

¥diluted with a thinning solution containing 1:1:1 distilled water/witch hazel extract/glycerine by weight.

Pigment Blue 15

Pigment Identity: Blue 15; Blue 15:3; CI 74160; Blue Phthalocyanine

Base Color Shade: Blue

TABLE 14

Blue Pigment Dispersion Formulation

| Chemical | EC Number | CAS Number | Percentage |
| --- | --- | --- | --- |
| CI 74160 | 205-685-1 | 147-14-8 | 20-40% |
| Distilled Water | 231-791-2 | 7732-18-5 | 20-40% |
| *Hamamelis Virginiana* Extract | 283-637-9 | 84696-19-5 | 10-25% |
| Ammonium Acrylates Copolymer | Not Registered | 63744-68-3 | 1-5% |
| Glycerine | 200-289-5 | 56-81-5 | 1-5% |
| Propylene Glycol | 200-338-0 | 57-55-6 | 1-5% |
| Ethyl Alcohol | 200-578-6 | 64-17-5 | 1-5% |
| D-Glucopyranose, oligomeric, C10-16-alkyl glycosides | 600-975-8 | 110615-47-9 | 1-5% |
| D-Glucopyranose, oligomers, decyl octyl glycosides | 500-220-1 | 68515-73-1 | 1-5% |
| Simethicone | 617-098-1 | 8050-81-5 | <1% |

Figure 3:
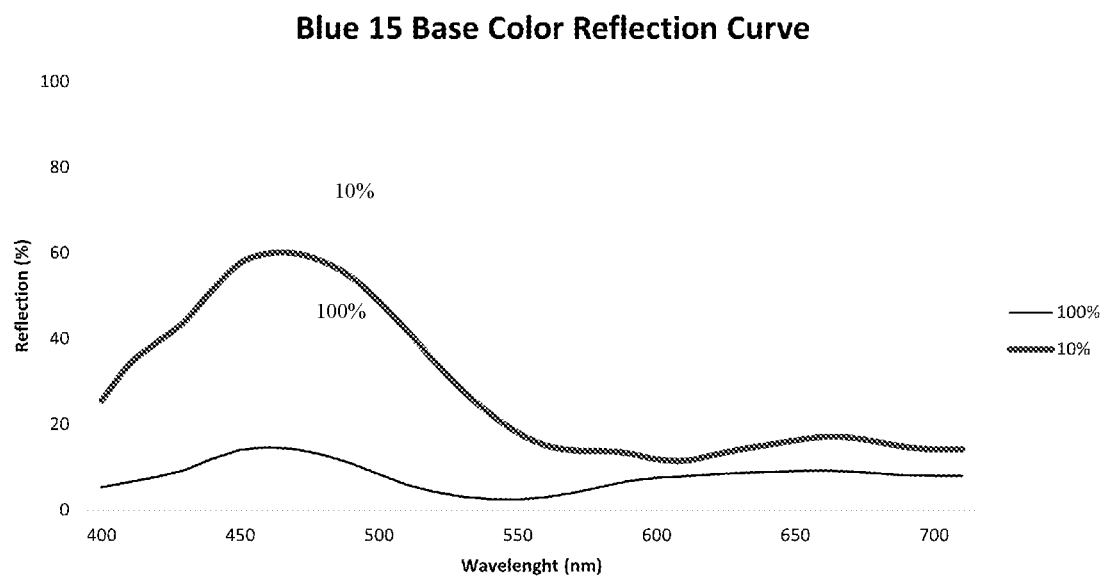
FIG. 3 is a graph of the color reflection curve for a pigment dispersion containing Blue 15.

The Blue 15 pigment dispersion processed by the method above has a reflection curve shown in FIG. 3 and CIE LAB values as shown in Table 15.

TABLE 15

Blue 15 Dispersion CIE LAB Values

| Ink Concentration (wt/wt) | L* | a* | b* | C* | h* |
| --- | --- | --- | --- | --- | --- |
| 100% | 28.67 | 14.31 | -22.18 | 26.40 | 302.83 |
| 10%¥ | 56.61 | -13.37 | -34.01 | 36.54 | 248.54 |

¥diluted with a thinning solution containing 1:1:1 distilled water/witch hazel extract/glycerine by weight.

Pigment Orange 64

Pigment Identity: Orange 64; CI 12760

Base Color Shade: Orange

TABLE 16

Orange 64 Pigment Dispersion Formulation

| Chemical | EC Number | CAS Number | Percentage |
| --- | --- | --- | --- |
| CI 12760 | 276-344-2 | 72102-84-2 | 20-40% |
| Distilled Water | 231-791-2 | 7732-18-5 | 20-40% |
| *Hamamelis Virginiana* Extract | 283-637-9 | 84696-19-5 | 10-25% |
| Ammonium Acrylates Copolymer | Not Registered | 63744-68-3 | 1-5% |
| Glycerine | 200-289-5 | 56-81-5 | 1-5% |
| Propylene Glycol | 200-338-0 | 57-55-6 | 1-5% |
| Ethyl Alcohol | 200-578-6 | 64-17-5 | 1-5% |
| D-Glucopyranose, oligomeric, C10-16-alkyl glycosides | 600-975-8 | 110615-47-9 | 1-5% |
| D-Glucopyranose, oligomers, decyl octyl glycosides | 500-220-1 | 68515-73-1 | 1-5% |
| Simethicone | 617-098-1 | 8050-81-5 | <1% |

Figure 4:
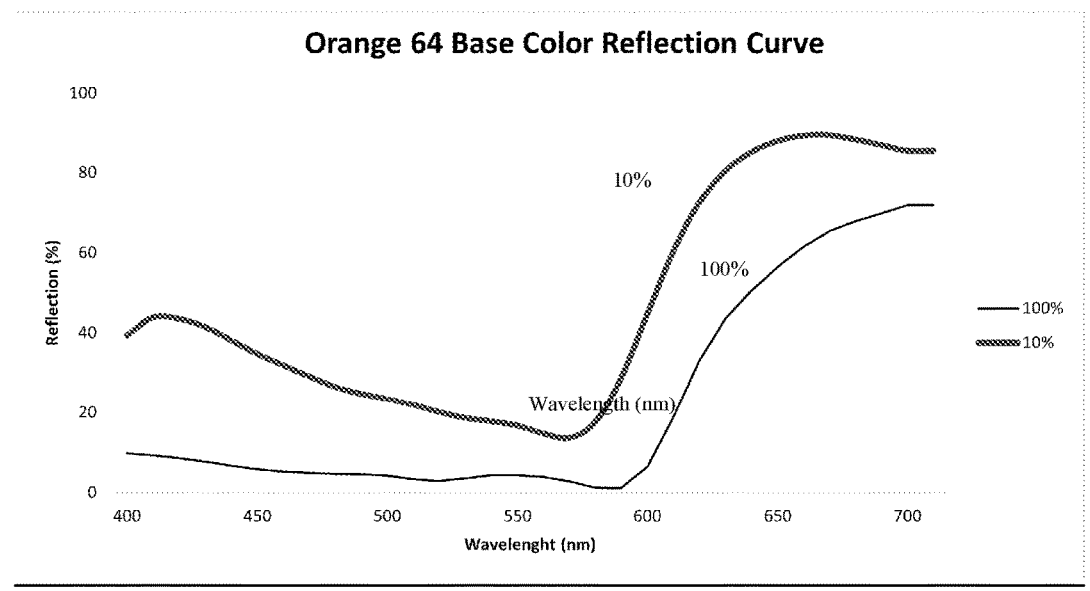
FIG. 4 is a graph of the color reflection curve for a pigment dispersion containing Orange 64.

The Orange 64 pigment dispersion processed by the method above has a reflection curve shown in FIG. 4 and CIE LAB values as shown in Table 17. In the preparation of Orange 64 pigment dispersion, careful consideration is taken to ensure that the temperature of the mixing vessel in the initial mixing step, i.e., before adding the pigment, does not reach 110° F. as the dissolution of pigment Orange 64 is exothermic.

TABLE 17

Orange 64 Dispersion CIE LAB Values

| Ink Concentration (wt/wt) | L* | a* | b* | C* | h* |
| --- | --- | --- | --- | --- | --- |
| 100% | 62.21 | 56.02 | 60.13 | 82.18 | 47.03 |
| 10%¥ | 73.89 | 40.54 | 47.92 | 62.77 | 49.77 |

¥diluted with a thinning solution containing 1:1:1 distilled water/witch hazel extract/glycerine by weight.

Pigment Red 202

Pigment Identity: Red 202; CI 73907

Base Color Shade: Magenta

TABLE 18

Red 202 Pigment Dispersion Formulation

| Chemical | EC Number | CAS Number | Percentage |
| --- | --- | --- | --- |
| CI 73907 | 221-424-4 | 3089-17-6 | 20-40% |
| Distilled Water | 231-791-2 | 7732-18-5 | 20-40% |
| *Hamamelis Virginiana* Extract | 283-637-9 | 84696-19-5 | 10-25% |
| Ammonium Acrylates Copolymer | Not Registered | 63744-68-3 | 1-5% |
| Glycerine | 200-289-5 | 56-81-5 | 1-5% |

TABLE 18-continued

Red 202 Pigment Dispersion Formulation

| Chemical | EC Number | CAS Number | Percentage |
|---|---|---|---|
| Propylene Glycol | 200-338-0 | 57-55-6 | 1-5% |
| Ethyl Alcohol | 200-578-6 | 64-17-5 | 1-5% |
| D-Glucopyranose, oligomeric, C10-16-alkyl glycosides | 600-975-8 | 110615-47-9 | 1-5% |
| D-Glucopyranose, oligomers, decyl octyl glycosides | 500-220-1 | 68515-73-1 | 1-5% |
| Simethicone | 617-098-1 | 8050-81-5 | <1% |

Figure 5:
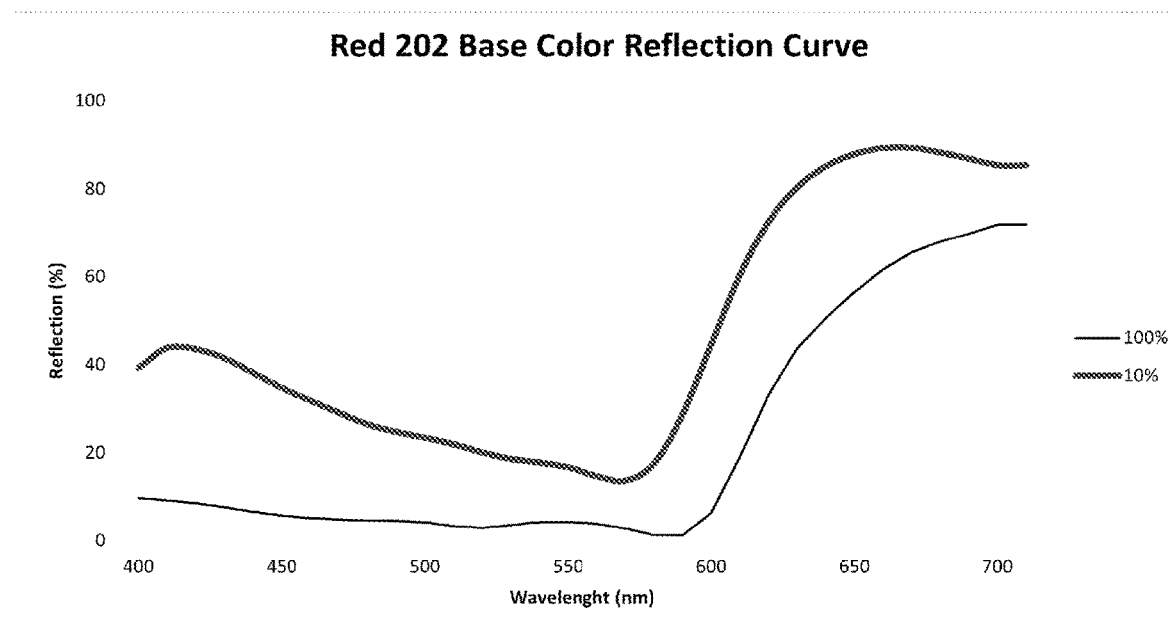
FIG. 5 is a graph of the color reflection curve for a pigment dispersion containing Red 202.

The Red 202 pigment dispersion processed by the method above has a reflection curve shown in FIG. 5 and CIE LAB values as shown in Table 19.

TABLE 19

Red 202 Dispersion CIE LAB Values

| Ink Concentration (wt/wt) | L* | a* | b* | C* | h* |
|---|---|---|---|---|---|
| 100% | 36.08 | 51.89 | 1.68 | 51.92 | 1.85 |
| 10%¥ | 57.20 | 46.12 | −10.99 | 47.41 | 346.60 |

¥diluted with a thinning solution containing 1:1:1 distilled water/witch hazel extract/glycerine by weight.

Pigment Red 254
Pigment Identity: Red 254; CI 56110
Base Color Shade: Red

TABLE 20

Red 254 Pigment Dispersion Formulation

| Chemical | EC Number | CAS Number | Percentage |
|---|---|---|---|
| CI 56110 | 401-540-3 | 84632-65-5 | 20-40% |
| Distilled Water | 231-791-2 | 7732-18-5 | 20-40% |
| *Hamamelis Virginiana* Extract | 283-637-9 | 84696-19-5 | 10-25% |
| Ammonium Acrylates Copolymer | Not Registered | 63744-68-3 | 1-5% |
| Glycerine | 200-289-5 | 56-81-5 | 1-5% |
| Propylene Glycol | 200-338-0 | 57-55-6 | 1-5% |
| Ethyl Alcohol | 200-578-6 | 64-17-5 | 1-5% |
| D-Glucopyranose, oligomeric, C10-16-alkyl glycosides | 600-975-8 | 110615-47-9 | 1-5% |
| D-Glucopyranose, oligomers, decyl octyl glycosides | 500-220-1 | 68515-73-1 | 1-5% |
| Simethicone | 617-098-1 | 8050-81-5 | <1% |

Figure 6:
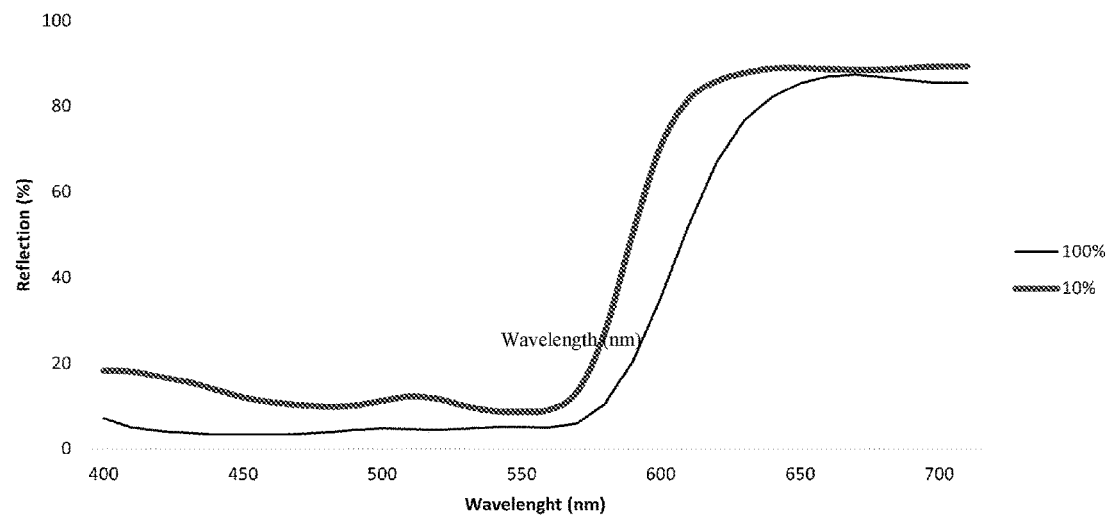
FIG. 6 is a graph of the color reflection curve for a pigment dispersion containing Red 254.

The Red 254 pigment dispersion processed by the method above has a reflection curve shown in FIG. 6 and CIE LAB values as shown in Table 21.

TABLE 21

Red 254 Dispersion CIE LAB Values

| Ink Concentration (wt/wt) | L* | a* | b* | C* | h* |
|---|---|---|---|---|---|
| 100% (red curve) | 45.95 | 56.37 | 40.53 | 69.43 | 35.72 |
| 10%¥ | 58.15 | 55.77 | 27.50 | 62.18 | 26.20 |

¥diluted with a thinning solution containing 1:1:1 distilled water/witch hazel extract/glycerine by weight.

Pigment Yellow 151
Pigment Identity: Yellow 151; CI 13980
Base Color Shade: Yellow

TABLE 22

Yellow 151 Pigment Dispersion Formulation

| Chemical | EC Number | CAS Number | Percentage |
|---|---|---|---|
| CI 13980 | 250-830-4 | 31837-42-0 | 20-40% |
| Distilled Water | 231-791-2 | 7732-18-5 | 20-40% |
| *Hamamelis Virginiana* Extract | 283-637-9 | 84696-19-5 | 10-25% |
| Ammonium Acrylates Copolymer | Not Registered | 63744-68-3 | 1-5% |
| Glycerine | 200-289-5 | 56-81-5 | 1-5% |
| Propylene Glycol | 200-338-0 | 57-55-6 | 1-5% |
| Ethyl Alcohol | 200-578-6 | 64-17-5 | 1-5% |
| D-Glucopyranose, oligomeric, C10-16-alkyl glycosides | 600-975-8 | 110615-47-9 | 1-5% |
| D-Glucopyranose, oligomers, decyl octyl glycosides | 500-220-1 | 68515-73-1 | 1-5% |
| Simethicone | 617-098-1 | 8050-81-5 | <1% |

Figure 7:
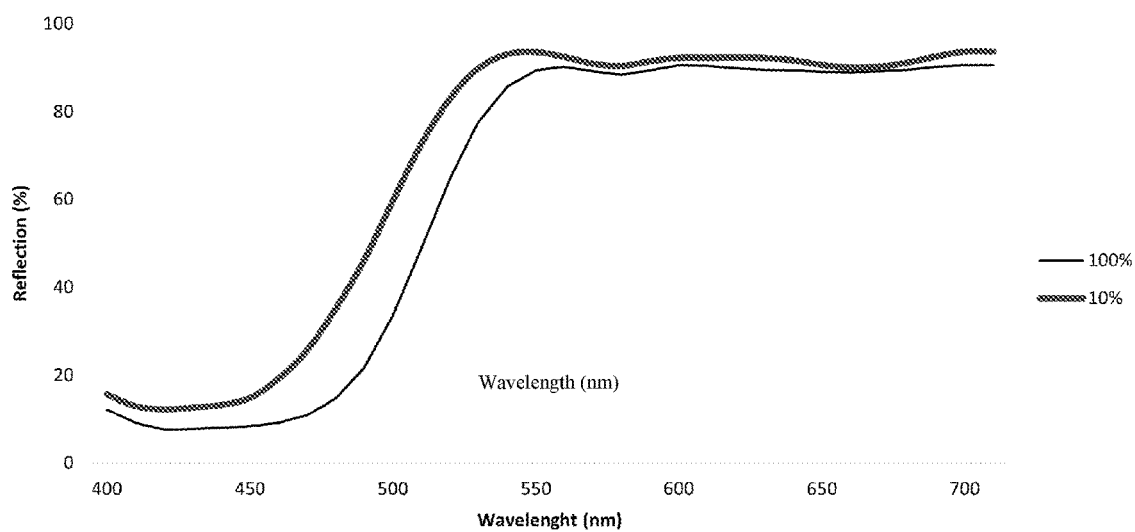
FIG. 7 is a graph of the color reflection curve for a pigment dispersion containing Yellow 151.

The Yellow 151 pigment dispersion processed by the method above has a reflection curve shown in FIG. 7 and CIE LAB values as shown in Table 23.

TABLE 23

Yellow 151 Dispersion CIE LAB Values

| Ink Concentration (wt/wt) | L* | a* | b* | C* | h* |
|---|---|---|---|---|---|
| 100% | 88.78 | −0.41 | 84.68 | 84.68 | 90.28 |
| 10%¥ | 92.67 | −9.08 | 68.68 | 69.27 | 97.53 |

¥diluted with a thinning solution containing 1:1:1 distilled water/witch hazel extract/glycerine by weight.

Pigment Yellow 180
Pigment Identity: Yellow 180; CI 21290
Base Color Shade: Yellow

TABLE 24

Yellow 180 Pigment Dispersion Formulation

| Chemical | EC Number | CAS Number | Percentage |
|---|---|---|---|
| CI 21290 | 278-770-4 | 77804-81-0 | 20-40% |
| Distilled Water | 231-791-2 | 7732-18-5 | 20-40% |
| *Hamamelis Virginiana* Extract | 283-637-9 | 84696-19-5 | 10-25% |
| Ammonium Acrylates Copolymer | Not Registered | 63744-68-3 | 1-5% |
| Glycerine | 200-289-5 | 56-81-5 | 1-5% |
| Propylene Glycol | 200-338-0 | 57-55-6 | 1-5% |
| Ethyl Alcohol | 200-578-6 | 64-17-5 | 1-5% |
| D-Glucopyranose, oligomeric, C10-16-alkyl glycosides | 600-975-8 | 110615-47-9 | 1-5% |
| D-Glucopyranose, oligomers, decyl octyl glycosides | 500-220-1 | 68515-73-1 | 1-5% |
| Simethicone | 617-098-1 | 8050-81-5 | <1% |

Figure 8:
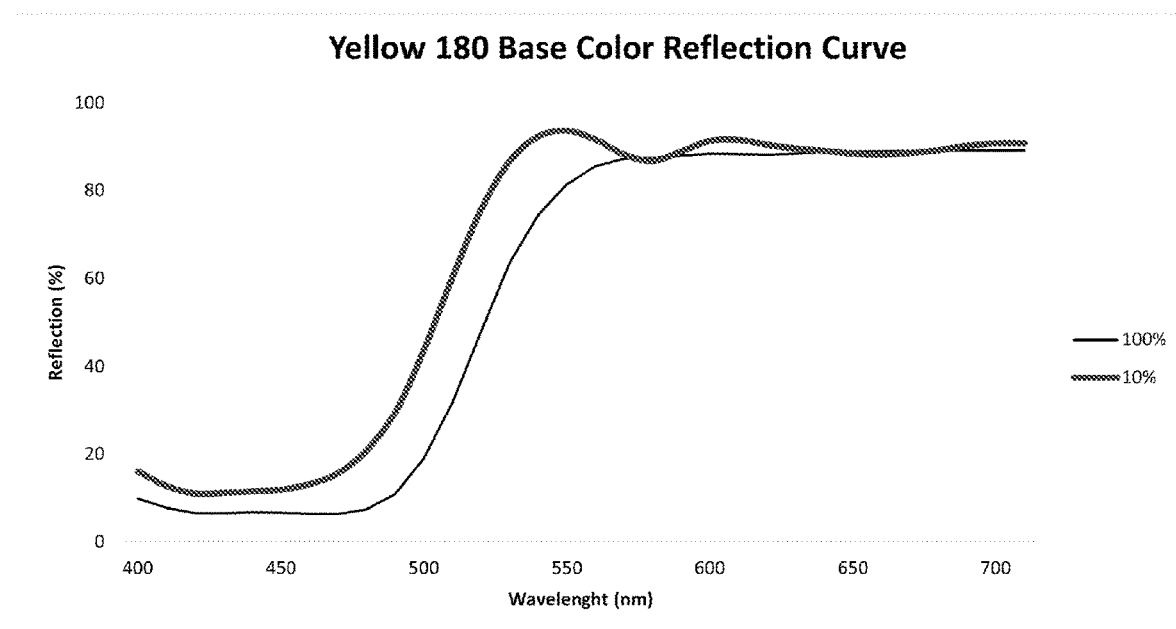
FIG. 8 is a graph of the color reflection curve for a pigment dispersion containing Yellow 180.

The Yellow 180 pigment dispersion processed by the method above has a reflection curve shown in FIG. 8 and CIE LAB values as shown in Table 25.

TABLE 25

Yellow 180 Dispersion CIE LAB Values

| Ink Concentration (wt/wt) | L* | a* | b* | C* | h* |
|---|---|---|---|---|---|
| 100% | 85.21 | 8.55 | 89.22 | 89.63 | 84.53 |
| 10%¥ | 90.68 | −5.49 | 76.73 | 76.92 | 94.09 |

¥diluted with a thinning solution containing 1:1:1 distilled water/witch hazel extract/glycerine by weight.

Pigment White 6
Pigment Identity: White 6; Titanium Dioxide; CI 77891
Base Color Shade: White

TABLE 26

White Pigment Dispersion Formulation

| Chemical | EC Number | CAS Number | Percentage |
|---|---|---|---|
| CI 77891 | 236-675-5 | 13463-67-7 | 30-60% |
| Distilled Water | 231-791-2 | 7732-18-5 | 20-40% |
| Hamamelis Virginiana Extract | 283-637-9 | 84696-19-5 | 10-25% |
| Ammonium Acrylates Copolymer | Not Registered | 63744-68-3 | 1-5% |
| Glycerine | 200-289-5 | 56-81-5 | 1-5% |
| Propylene Glycol | 200-338-0 | 57-55-6 | 1-5% |
| Ethyl Alcohol | 200-578-6 | 64-17-5 | 1-5% |
| D-Glucopyranose, oligomeric, C10-16-alkyl glycosides | 600-975-8 | 110615-47-9 | 1-5% |
| D-Glucopyranose, oligomers, decyl octyl glycosides | 500-220-1 | 68515-73-1 | 1-5% |
| Simethicone | 617-098-1 | 8050-81-5 | <1% |

Figure 9:
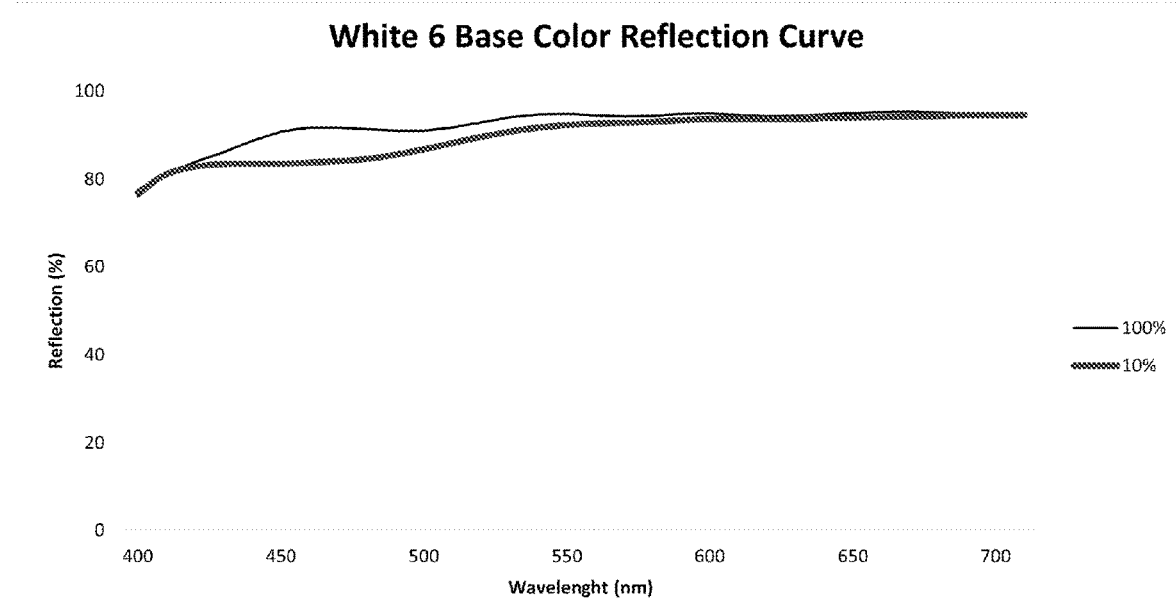
FIG. 9 is a graph of the color reflection curve for a pigment dispersion containing White 6.

The White 6 pigment dispersion processed by the method above has a reflection curve shown in FIG. 9 and CIE LAB values as shown in Table 27.

TABLE 27

White 6 Dispersion CIE LAB Values

| Ink Concentration (wt/wt) | L* | a* | b* | C* | h* |
|---|---|---|---|---|---|
| 100% | 95.99 | −0.77 | 2.72 | 2.82 | 105.74 |
| 10%¥ | 94.54 | −0.06 | 4.38 | 4.38 | 90.76 |

¥diluted with a thinning solution containing 1:1:1 distilled water/witch hazel extract/glycerine by weight.

Pigment Blue 60
Pigment Identity: Blue 60; CI 69800
Base Color Shade: Blue

TABLE 28

Blue 60 Dispersion Formula

| Chemical | EC Number | CAS Number | Percentage |
|---|---|---|---|
| CI 69800 | 201-375-5 | 81-77-6 | 20-40% |
| Distilled Water | 231-791-2 | 7732-18-5 | 20-40% |
| Hamamelis Virginiana Extract | 283-637-9 | 84696-19-5 | 10-25% |
| Ammonium Acrylates Copolymer | Not Registered | 63744-68-3 | 1-10% |
| Glycerine | 200-289-5 | 56-81-5 | 1-5% |
| Propylene Glycol | 200-338-0 | 57-55-6 | 1-5% |
| Ethyl Alcohol | 200-578-6 | 64-17-5 | 1-5% |
| D-Glucopyranose, oligomeric, C10-16-alkyl glycosides | 600-975-8 | 110615-47-9 | 1-5% |
| D-Glucopyranose, oligomers, decyl octyl glycosides | 500-220-1 | 68515-73-1 | 1-5% |
| Simethicone | 617-098-1 | 8050-81-5 | <1% |

Figure 10:
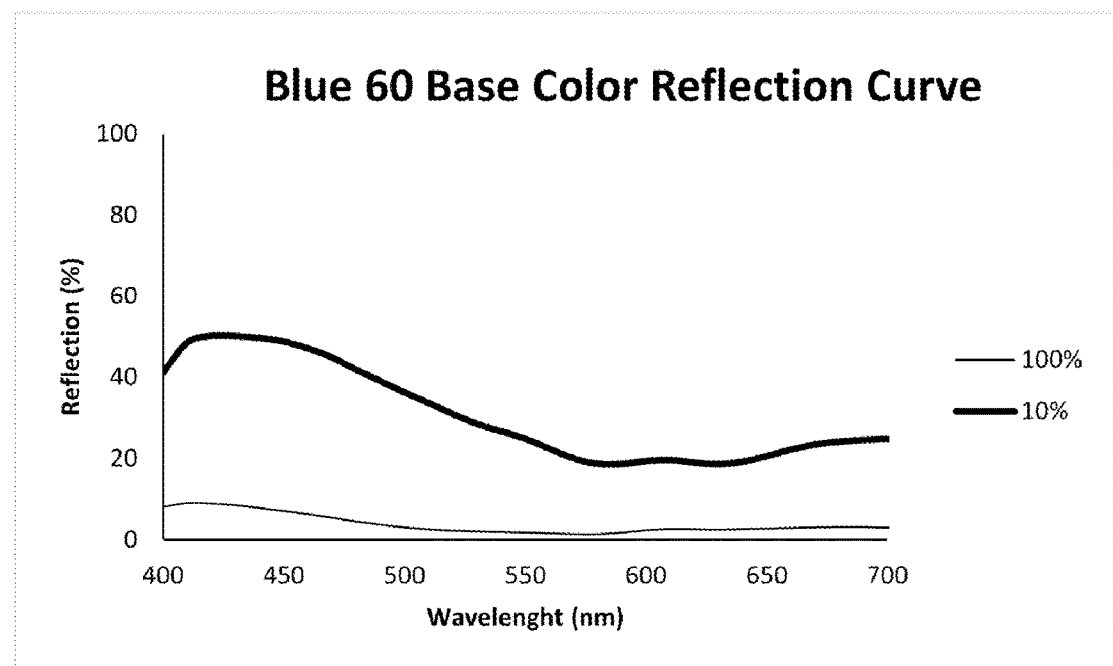
FIG. 10 is a graph of the color reflection curve for a pigment dispersion containing Blue 60.

The Blue 60 pigment dispersion was processed by the method above except that complete particle size reduction was achieved by using an in-line high shear mixer, passing the mixture through a media mill. Blue 60 pigment dispersion has a reflection curve shown in FIG. 10 and CIE LAB values as shown in Table 29.

TABLE 29

Blue 60 Dispersion CIE LAB Values

| Ink Concentration (wt/wt) | L* | a* | b* | C* | h* |
|---|---|---|---|---|---|
| 100% | 17.82 | 12.03 | −23.58 | 26.47 | 297.02 |
| 10%¥ | 58.43 | −2.06 | −27.08 | 27.16 | 265.65 |

¥diluted with a thinning solution containing 1:1:1 distilled water/witch hazel extract/glycerine by weight.

Pigment Blue 16
Pigment Identity: Blue 16; CI 74100
Base Color Shade: Blue

TABLE 30

Blue 16 Dispersion Formula

| Chemical | EC Number | CAS Number | Percentage |
|---|---|---|---|
| CI 74100 | 209-378-3 | 574-93-6 | 20-40% |
| Distilled Water | 231-791-2 | 7732-18-5 | 20-40% |
| Hamamelis Virginiana Extract | 283-637-9 | 84696-19-5 | 10-25% |
| Ammonium Acrylates Copolymer | Not Registered | 63744-68-3 | 1-10% |
| Glycerine | 200-289-5 | 56-81-5 | 1-5% |
| Propylene Glycol | 200-338-0 | 57-55-6 | 1-5% |
| Ethyl Alcohol | 200-578-6 | 64-17-5 | 1-5% |
| D-Glucopyranose, oligomeric, C10-16-alkyl glycosides | 600-975-8 | 110615-47-9 | 1-5% |
| D-Glucopyranose, oligomers, decyl octyl glycosides | 500-220-1 | 68515-73-1 | 1-5% |
| Simethicone | 617-098-1 | 8050-81-5 | <1% |

Figure 11:
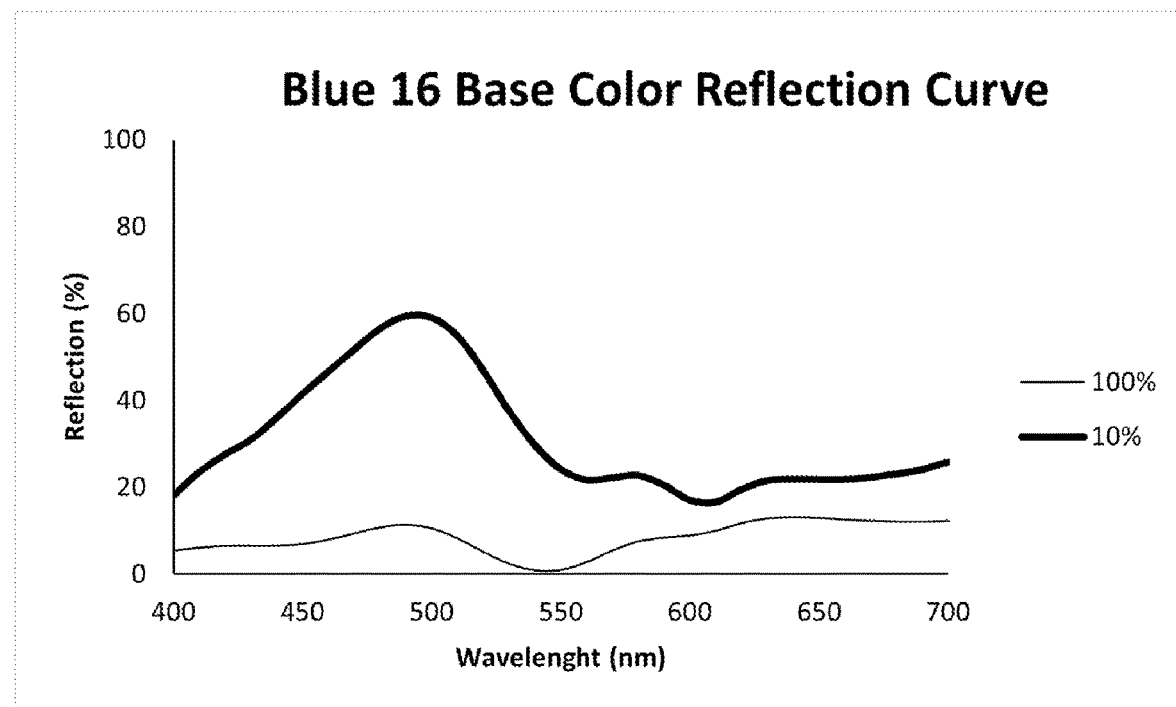
FIG. 11 is a graph of the color reflection curve for a pigment dispersion containing Blue 16.

The Blue 16 pigment dispersion processed by the method above has a reflection curve shown in FIG. 11 and CIE LAB values as shown in Table 31.

TABLE 31

Blue 16 Dispersion CIE LAB Values

| Ink Concentration (wt/wt) | L* | a* | b* | C* | h* |
|---|---|---|---|---|---|
| 100% | 30.08 | 14.44 | −5.87 | 15.59 | 337.88 |
| 10%¥ | 63.22 | −25.32 | −13.26 | 28.59 | 207.64 |

¥diluted with a thinning solution containing 1:1:1 distilled water/witch hazel extract/glycerine by weight.

Pigment Green 36
Pigment Identity: Green 36; CI 74265
Base Color Shade: Green

TABLE 32

Green 36 Dispersion Formula

| Chemical | EC Number | CAS Number | Percentage |
|---|---|---|---|
| CI 74265 | 238-238-4 | 14302-13-7 | 20-40% |
| Distilled Water | 231-791-2 | 7732-18-5 | 20-40% |
| Hamamelis Virginiana Extract | 283-637-9 | 84696-19-5 | 10-25% |
| Ammonium Acrylates Copolymer | Not Registered | 63744-68-3 | 1-10% |
| Glycerine | 200-289-5 | 56-81-5 | 1-5% |
| Propylene Glycol | 200-338-0 | 57-55-6 | 1-5% |
| Ethyl Alcohol | 200-578-6 | 64-17-5 | 1-5% |
| D-Glucopyranose, oligomeric, C10-16-alkyl glycosides | 600-975-8 | 110615-47-9 | 1-5% |
| D-Glucopyranose, oligomers, decyl octyl glycosides | 500-220-1 | 68515-73-1 | 1-5% |
| Simethicone | 617-098-1 | 8050-81-5 | <1% |

Figure 12:
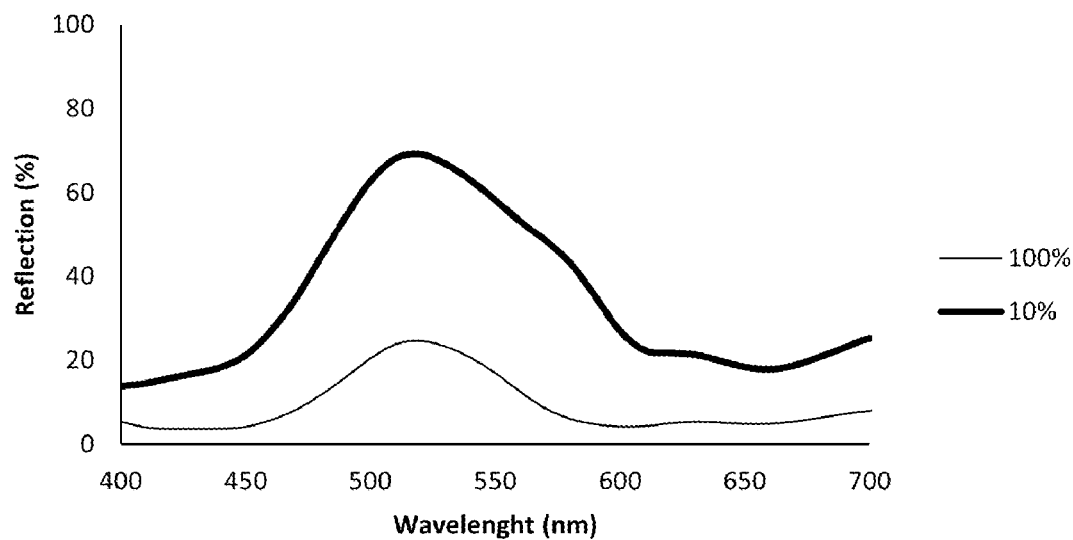
FIG. 12 is a graph of the color reflection curve for a pigment dispersion containing Green 36.

The Green 36 pigment dispersion is processed by the method above and has a reflection curve shown in FIG. 12 and CIE LAB values as shown in Table 33.

TABLE 33

Green 36 Dispersion CIE LAB Values

| Ink Concentration (wt/wt) | L* | a* | b* | C* | h* |
|---|---|---|---|---|---|
| 100% | 43.59 | −44.07 | 22.30 | 49.39 | 153.16 |
| 10%¥ | 75.55 | −45.53 | 28.85 | 52.22 | 146.46 |

¥diluted with a thinning solution containing 1:1:1 distilled water/witch hazel extract/glycerine by weight.

Pigment Green 7

Pigment Identity: Green 7; CI 74260

Base Color Shade: Green

TABLE 34

Green 7 Dispersion Formula

| Chemical | EC Number | CAS Number | Percentage |
|---|---|---|---|
| CI 74260 | 215-524-7 | 1328-53-6 | 20-50% |
| Distilled Water | 231-791-2 | 7732-18-5 | 20-40% |
| Hamamelis Virginiana Extract | 283-637-9 | 84696-19-5 | 10-25% |
| Ammonium Acrylates Copolymer | Not Registered | 63744-68-3 | 1-10% |
| Glycerine | 200-289-5 | 56-81-5 | 1-5% |
| Propylene Glycol | 200-338-0 | 57-55-6 | 1-5% |
| Ethyl Alcohol | 200-578-6 | 64-17-5 | 1-5% |
| D-Glucopyranose, oligomeric, C10-16-alkyl glycosides | 600-975-8 | 110615-47-9 | 1-5% |
| D-Glucopyranose, oligomers, decyl octyl glycosides | 500-220-1 | 68515-73-1 | 1-5% |
| Simethicone | 617-098-1 | 8050-81-5 | <1% |

Figure 13:
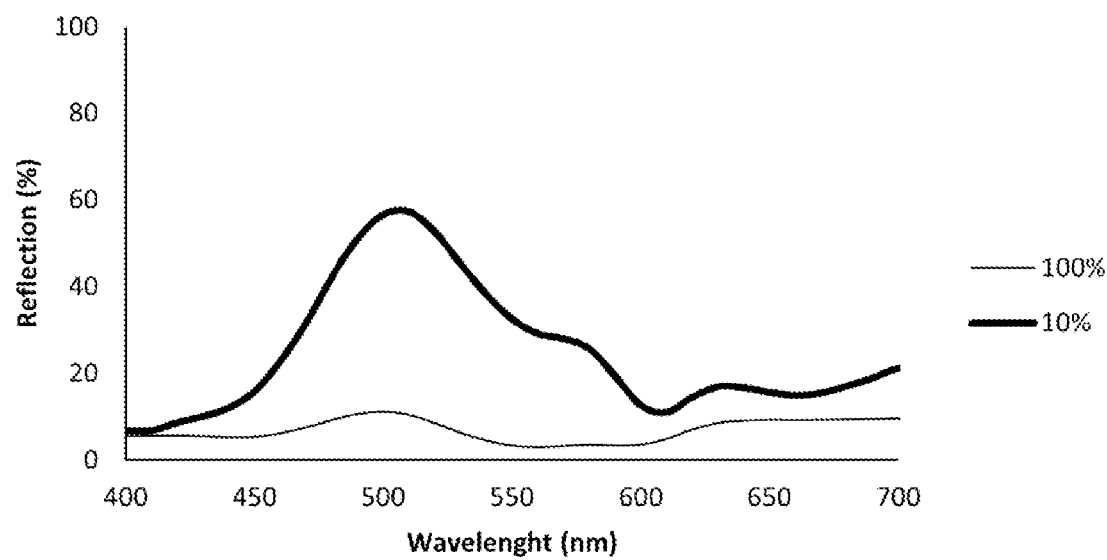
FIG. 13 is a graph of the color reflection curve for a pigment dispersion containing Green 7.

The Green 7 pigment dispersion is processed by the method above and has a reflection curve shown in FIG. 13 and CIE LAB values as shown in Table 35.

TABLE 35

Green 7 Dispersion CIE LAB Values

| Ink Concentration (wt/wt) | L* | a* | b* | C* | h* |
|---|---|---|---|---|---|
| 100% | 28.82 | −7.26 | −2.98 | 7.85 | 202.33 |
| 10%¥ | 64.17 | −46.92 | 18.54 | 50.45 | 158.44 |

¥diluted with a thinning solution containing 1:1:1 distilled water/witch hazel extract/glycerine by weight.

While there have been described what are presently believed to be various aspects and certain desirable embodiments of the disclosure, those skilled in the art will recognize that changes and modifications may be made thereto without departing from the spirit of the disclosure, and it is intended to include all such changes and modifications as fall within the true scope of the disclosure.

What is claimed:
1. A pigment dispersion comprising:
 a pigment selected from the group consisting of Blue 16, Blue 60, Green 36, Green 7, and any combination thereof;
 one or more solvents comprising *Hamamelis virginiana* extract;
 a wetting agent comprising one or more alkyl polyglycosides;
 an antifoaming agent;
 ammonium acrylate copolymer in about 1% to about 20% by weight of the total pigment dispersion;
 and one or more additives selected from a group consisting of: a dispersant, a binding agent, a humectant, and any combination thereof;
 wherein the alkyl polyglycosides is present in about 10% to about 15% by weight of the total pigment dispersion, and wherein the content of the *Hamamelis virginiana* extract ranges from about 15% to about 25% by weight of the total pigment dispersion.
2. The pigment dispersion of claim 1, wherein the one or more solvents further comprises ethyl alcohol, and water.
3. The pigment dispersion of claim 1, wherein the one or more additives in the pigment dispersion comprise a dispersant and a humectant.
4. The pigment dispersion of claim 1, wherein the pigment dispersion contains about 30 wt. % to about 60 wt. % pigment.
5. The pigment dispersion of claim 1, wherein the pigment dispersion contains less than about 0.5 ppm of each of: Naphthalene, Acenaphthalene. Acenaphthene, Fluorene, Phenanthrene, Anthracene, Fluoranthene, Pyrene, Benzo[a]anthracene, Chrysene, Benzo[b]fluoranthene, Benzo[k]fluoranthene, Benzo[ghi]perylene, Dibenzo[ah]anthracene, Indeno[1,2,3,cd]pyrene, Cyclopenta[cd]pyrene, Benzo[j]fluoranthene, Benzo[e]pyrene, Dibenzo[ai]pyrene, Dibenzo[a]pyrene, Dibenzo[ae]pyrene, Benzo[c]fluorene, Dibenzo[ah]pyrene, 1-Methylpyrene, and 5-Methylchrysene.
6. The pigment dispersion of claim 1, comprising one or more of the following:
 less than about 0.5 ppm of mercury, organometallic tin, antimony, arsenic, cadmium, chromium (Cr (VI)), or any combination thereof;
 less than about 0.7 ppm of lead;
 less than about 5 ppm of nickel;
 less than about 500 ppm of barium;
 less than about 250 ppm of copper;
 less than about 2 ppm of selenium;
 less than about 2000 ppm of zinc; and
 less than 0.005 ppm of benz[a]pyrene.

7. The pigment dispersion of claim 1, wherein the pigment dispersion contains less than about 5 ppm of one or more of the following free aromatic amines: 4-Aminobiphenyl, Benzidine, 4-Chloro-o-toluidine, 2-Naphtylamine, 4-o-Tolylazo-o-toluidin, 5-Nitro -o-toluidine, 4-Chloroaniline, 4-Methoxy-m-phenylendiamine, 4,4'-Methylenedianiline, 3,3'-Dichlorobenzidine, 3,3'-Dimethoxybenzidine, 4,4'-Bio-Toluidin, 4,4'-Methylenedi-o-toluidine, 6-Methoxy-m-toluidine, 4,4'-Methylenebis-(2-chloroaniline), 4-Methyl-m-phenylenediamine, o -Anisidine, 4-Aminoazobenzene, 2-Methyl-p-phenylendiamin, 4-Amino-3-florophenol, 4,4'-Oxydianilinie,4,4'-Thiodianiline, o-Toluidine, 2,4,5-Trimethylaniline, p-Phenylendiamine, Aniline, p-Toluidine, Sulfanilic acid, 2,6-Xylidine, 6-Amino-2-ethoxynaphtaline, and 2,4-Xylidine.

8. The pigment dispersion of claim 1, wherein the pigment particle size distribution D90 of the pigment dispersion is less than about 5 μm.

9. A tattoo ink formulation comprising:
a pigment dispersion of claim 1; and
an additional solvent comprising *Hamamelis virginiana* Extract.

10. The tattoo ink formulation of claim 9, wherein the pigment dispersion comprises less than about 95 wt. % of the tattoo ink formulation.

11. The tattoo ink formulation of claim 9, comprising: about 1 wt. % to about 95 wt. % of the pigment dispersion; about 1 wt. % to about 50 wt. % of *Hamamelis virginiana* Extract; and about 1 wt. % to about 50 wt. % water by weight of the total tattoo ink formulation.

12. The tattoo ink formulation of claim 9, comprising less than about 5 wt. % of impurities.

13. The tattoo ink formulation of claim 9, comprising: less than or equal to about 0.5 ppm total polycyclic aromatic hydrocarbons; less than or equal to about 10 ppm benzo[a] pyrene (BaP); less than or equal to about 10 ppm dibenz[a, h]anthracene (DBA); less than or equal to about 3 ppm arsenic; less than or equal to about 1 ppm mercury; and/or less than or equal to about 10 ppm lead.

14. A pigment dispersion comprising:
a pigment consisting of Blue 60 in about 20% to about 40% by weight of the total dispersion;
*Hamamelis virginiana* extract in about 10% to about 25% by weight of the total dispersion;
ethyl alcohol in about 1% to about 5% by weight of the total dispersion;
alkyl polyglycosides in about 10% to about 15% by weight of the total dispersion;
ammonium acrylate copolymer in about 1% to about 10% by weight of the total dispersion;
an antifoaming agent;
and one or more additives
selected from a group consisting of: a dispersant, a binding agent, a humectant, and any combination thereof.

15. The pigment dispersion of claim 14, wherein the pigment dispersion has a CIE LAB value at 100% (wt/wt) of L*=17.82, a*=12.03 and b*=-23.58.

16. The pigment dispersion of claim 14, wherein the pigment particle size range of the pigment dispersion is about 60 nm to about 15 μm.

17. A tattoo ink formulation comprising:
a pigment dispersion of claim 14; and
an additional solvent comprising *Hamamelis virginiana* Extract.

18. A method of making the pigment dispersion of claim 14, comprising mixing the pigment, one or more solvents, and one or more additives using an in-line high shear mixer for a period of about 30 minutes to about 4 hours at a speed of about 1,000 feet per minute to about 20,000 feet per minute.

19. A pigment dispersion comprising:
a pigment consisting of Green 36 in about 20% to about 40% by weight of the total dispersion;
*Hamamelis virginiana* extract in about 10% to about 25% by weight of the total dispersion;
ethyl alcohol in about 1% to about 5% by weight of the total dispersion;
alkyl polyglycosides in about 10% to about 15% by weight of the total dispersion;
ammonium acrylate copolymer in about 1% to about 10% by weight of the total dispersion;
an antifoaming agent;
and one or more additives selected from a group consisting of: a dispersant, a binding agent, a humectant, and any combination thereof.

20. The pigment dispersion of claim 19, wherein the pigment dispersion has a CIE LAB value at 100% (wt/wt) of L*=43.59, a*=-44.07 and b*=22.30.

21. The pigment dispersion of claim 19, wherein the pigment particle size range of the pigment dispersion is about 60 nm to about 10 μm.

22. A tattoo ink formulation comprising:
a pigment dispersion of claim 19; and
an additional solvent comprising *Hamamelis virginiana* Extract.

* * * * *